US008578789B2

(12) United States Patent  (10) Patent No.: US 8,578,789 B2
Murata  (45) Date of Patent: Nov. 12, 2013

(54) ANALYSIS DEVICE AND ANALYSIS METHOD

(75) Inventor: Yasuhito Murata, Kyoto (JP)

(73) Assignee: Arkray, Inc., Kyoto (JP)

( * ) Notice: Subject to any disclaimer, the term of this patent is extended or adjusted under 35 U.S.C. 154(b) by 147 days.

(21) Appl. No.: 12/738,000

(22) PCT Filed: Sep. 17, 2009

(86) PCT No.: PCT/JP2009/066311
§ 371 (c)(1),
(2), (4) Date: Mar. 8, 2011

(87) PCT Pub. No.: WO2010/032804
PCT Pub. Date: Mar. 25, 2010

(65) Prior Publication Data
US 2011/0154910 A1    Jun. 30, 2011

(30) Foreign Application Priority Data

Sep. 17, 2008 (JP) ................................ 2008-237489

(51) Int. Cl.
G01F 1/708 (2006.01)
A61B 5/02 (2006.01)
A61B 5/026 (2006.01)
G01N 33/49 (2006.01)
G01N 35/08 (2006.01)

(52) U.S. Cl.
CPC ............ *A61B 5/02028* (2013.01); *A61B 5/026* (2013.01); *G01F 1/7086* (2013.01); *G01N 33/49* (2013.01); *G01N 35/08* (2013.01)
USPC .... 73/861.52; 73/861; 73/861.04; 73/861.05; 73/863

(58) Field of Classification Search
USPC ............... 73/861.05, 861.04, 861.52, 861.57, 73/861.63, 861.65, 32 R
See application file for complete search history.

(56) References Cited

U.S. PATENT DOCUMENTS 3,881,483 A * 5/1975 Sausse ......................... 604/6.14
5,023,054 A   6/1991 Sato et al.

FOREIGN PATENT DOCUMENTS

| JP | 02-130471 A | 5/1990 |
| JP | 11-118819 A | 4/1999 |
| JP | 2920379 B2  | 4/1999 |
| JP | 11-153462 A | 6/1999 |
| JP | 11-304561 A | 11/1999 |

OTHER PUBLICATIONS

International Search Report mailed on Dec. 22, 2009.

* cited by examiner

*Primary Examiner* — Hezron E Williams
*Assistant Examiner* — Alexander Mercado
(74) *Attorney, Agent, or Firm* — Rader, Fishman & Grauer PLLC

(57) ABSTRACT

An analysis method using an analysis apparatus are described herein. By way of an example, the analysis method includes a first step of driving a pressurizing pump and a pressure-reduction pump, and of filling a liquid from a supply piping in an interior of a resistive body through which a sample passes, a second step of discharging, from a discharging piping, some of the liquid filled in the interior of the resistive body, and of securing a space in the interior of the resistive body for filling the sample, a third step of supplying the sample into the space, a fourth step of causing the sample to travel in the interior of the resistive body, and a fifth step of measuring a travel time of the sample in the interior of the resistive body by using the flow rate sensor.

2 Claims, 32 Drawing Sheets

FIG.30A
FIG.30B
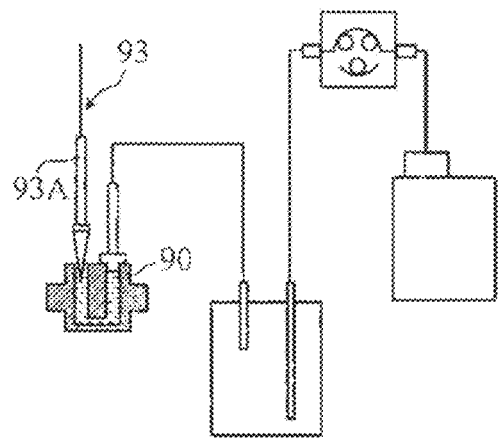
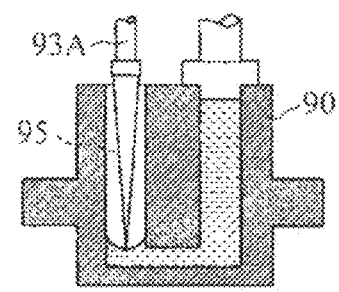

ANALYSIS DEVICE AND ANALYSIS METHOD

TECHNICAL FIELD

The present invention relates to a technology of inspecting a flow property of a sample. Also, the present invention relates to a technology of inspecting a flowability of a blood and a condition of a cell, such as a transformability and an activity of a cell in a blood using a resistive body like a blood filter as an example.

BACKGROUND ART

An example scheme of inspecting a flowability of a blood and a condition of a cell in the blood is a scheme of using a blood filter (see, for example, patent literatures 1 and 2). The blood filter includes a substrate formed with minute grooves and another substrate is joined with that substrate. When such a blood filter is used, a velocity when a blood passes through the grooves can be measured, or a condition of a cell in the blood when the blood passes through the grooves can be observed.

FIG. 28 is a piping diagram showing an illustrative blood inspecting apparatus using the blood filter. A blood inspecting apparatus 9 includes a liquid feeding mechanism 91, a liquid discharging mechanism 92, a blood supply mechanism 93 and a flow rate measuring mechanism 94.

The liquid feeding mechanism 91 is for supplying a predetermined liquid to a blood filter 90, and includes liquid reserving bottles 91A, 91B and a liquid feeding nozzle 91C. The liquid reserving bottle 91A reserves an isotonic sodium chloride solution for measurement. The liquid feeding mechanism 91 has the liquid reserving bottle 91 B for reserving a distilled water for rinsing. According to this liquid feeding mechanism 91, as a three-way valve 91D is switched accordingly with the liquid feeding nozzle 91C being attached to the liquid filter 90, a state in which the isotonic sodium chloride solution is supplied to the liquid feeding nozzle 91C and a state in which the distilled water is supplied to the liquid feeding nozzle 91C can be selected.

The liquid discharging mechanism 92 is for discharging a liquid in the blood filter 90, and includes a liquid discharging nozzle 92A, a pressure-reduction bottle 92B, a pressure-reduction pump 92C and a liquid discharging bottle 92D. According to this liquid discharging mechanism 92, as the pressure-reduction pump 92C is actuated with the liquid discharging nozzle 92A being attached to the blood filter 90, the liquid in the blood filter 90 is discharged in the pressure-reduction bottle 92B through a piping 92E. The liquid in the pressure-reduction bottle 92B is discharged in the liquid discharging bottle 92D through a piping 92F by the pressure-reduction pump 92B.

The blood supply mechanism 93 is for supplying a blood to the space formed by suctioning a liquid from the blood filter 90, and includes a sampling nozzle 93A.

The flow rate measuring mechanism 94 is for obtaining information necessary for measuring a speed of a blood travelling through the blood filter 90, and includes a U-tube 94A and a measuring nozzle 94B. The U-tube 94A is connected to the blood filter 90 by a piping 94C. The U-tube 94A is filled with a liquid, while the piping 94C is filled with air. A blood in the blood filter 90 is travelled by a water head difference between the blood filter 90 and the pressure-reduction bottle 92B.

According to the blood inspecting apparatus 9, a traveling time of a blood is measured as follows.

First, as shown in FIG. 29, the interior of the blood filter 90 is replaced with an isotonic sodium chloride solution. More specifically, the liquid feeding nozzle 91C of the liquid feeding mechanism 91 is attached to the blood filter 90, and the three-way valve 91D is switched so that an isotonic sodium chloride solution in the liquid reserving bottle 91A can be supplied to the liquid feeding nozzle 91C. On the other hand, the liquid discharging nozzle 92A of the liquid discharging mechanism 92 is attached to the blood filter 90, and the pressure-reduction pump 92C is actuated. Accordingly, the isotonic sodium chloride solution in the liquid reserving bottle 91A is supplied to the blood filter 90 through the liquid feeding nozzle 91C, and a waste liquid in the blood filter 90 is discharged in the liquid discharging bottle 92D through the liquid discharging nozzle 92A and the pressure-reduction bottle 92B.

Next, the liquid feeding nozzle 91C is detached from the blood filter 90, and as shown in FIG. 30A, some of the isotonic sodium chloride solution in the blood filter 90 are suctioned by the sampling nozzle 93A of the blood supply mechanism 93, and as shown in FIG. 30B, a space 95 for retaining a blood is formed.

Furthermore, as shown in FIG. 31A, a blood is collected from a blood collecting tube 96 by the sampling nozzle 93A, and as shown in FIG. 31B, a collected blood 97 is filled in the space 95 of the blood filter 90.

Subsequently, as shown in FIG. 32A, the measuring nozzle 94B of the flow rate measuring mechanism 94 is attached to the blood filter 90. Accordingly, as a water head difference caused between the blood filter 90 and the pressure-reduction bottle 92B, the blood in the blood filter 90 travels, and a liquid-level position in the U-tube 94A changes. According to the blood inspecting apparatus 9, as shown in FIG. 32B, a change speed of the liquid-level position in the U-tube 94A is detected by plural photo sensors 97, and based on the detection result, a travel time of the blood is calculated.

According to a scheme of connecting the U-tube 94A and the blood filter 90 together, however, because the liquid-level position in the U-tube 94A changes, a measurement pressure (a pressure which acts on the blood 97 in the blood filter 90) varies. Moreover, in order to cause the blood 97 to travel in the blood filter 90 by water head difference, it is necessary that the pipings 92E, 94C from the U-tube 94A and the blood filter 90 to the pressure-reduction bottle 92B must be filled with a liquid. Accordingly, because a relatively-long piping length is requisite, the piping resistance becomes large. Furthermore, in addition to the liquid feeding nozzle 91C and the liquid discharging nozzle 92A, the measurement nozzle 94B for connecting the U-tube 94A and the blood filter 90 is requisite, the number of nozzles necessary for a measurement becomes large. What is more, because the number of nozzles is large, the piping becomes complex, and the number of valves for switching the nozzles 91C, 92A, 93A, and 94B becomes large, so that the number of parts is large. This prohibits the miniaturization of the apparatus. The more the number of parts is, the more the number of parts like a valve which has a relatively large failure rate becomes, so that the mean-time-between-failure (MTBF) which is an index expressing a failure rate (performance) of the apparatus becomes short.

Moreover, according to a scheme of suctioning the isotonic sodium chloride solution from the blood filter 90 by using the sampling nozzle 93A before a blood is supplied to the blood filter 90, it is necessary to frequently switch the nozzles 91C, 92A, 93A, and 94B to use, so that a measurement time becomes long. In particular, in order to control the suction amount of the isotonic sodium chloride solution in an appropriate amount, it is necessary to suction the isotonic sodium chloride solution while appropriately monitoring the liquid level in the blood filter 90, so that it takes a lot of time for suctioning of the isotonic sodium chloride solution.

Furthermore, filling of the isotonic sodium chloride solution in the blood filter 90 is carried out by using the pressure-reduction pump 92C of the liquid discharging mechanism 92. However, air bubbles are likely to be mixed in the blood filter 90 by suctioning merely from the downstream side of the blood filter 90. In order to overcome such problem, it is necessary to cause the isotonic sodium chloride solution to flow into the blood filter 90 for a relatively long time by a high negative pressure. In this case, the amount of isotonic sodium chloride solution used becomes large, which is uneconomical, and the electric power consumption of the pressure-reduction pump becomes large, which is disadvantageous from the standpoint of a running cost.

Patent Literature 1: Unexamined Japanese Patent Application KOKAI Publication No. H02-130471

Patent Literature 2: Unexamined Japanese Patent Application KOKAI Publication No. H11-118819

DISCLOSURE OF INVENTION

Problem to be Solved by Invention

It is an object of the present invention to accomplish miniaturization of an apparatus by reducing the number of parts in a blood inspection using a blood filter, and to realize cost-down and extension of the mean-time-between-failure.

It is another object of the present invention to reduce a pressure variation and a resistance of a piping in an apparatus, and to accomplish improvement of a measurement precision, shortening of a measurement time, and reduction of the running cost.

Means for Solving the Problem

According to a first aspect of the present invention, there is provided an analysis apparatus that comprises a resistive body through which a sample passes and a flow rate sensor for measuring a travel time of the sample at the resistive body.

The flow rate sensor is arranged at a halfway of a discharging piping for discharging a liquid supplied to the resistive body.

The flow rate sensor includes a tubular body through which a liquid or a gas passes, and a sensor unit with a plurality of detecting areas for detecting an interface between the liquid and the air travelling in the tubular body. For example, the tubular body is a straight tube.

Preferably, the straight tube is arranged so as to run in the horizontal direction. The plural detecting areas are arranged side by side in the horizontal direction.

The analysis apparatus of the present invention may further comprise air inletting means for inletting air which travels in the tubular body.

The analysis apparatus of the present invention may further comprise a pressure-reduction pump which provides power to cause the liquid supplied to the resistive body to travel, and a pressure-reduction bottle provided between the tubular body and the pressure-reduction pump. In this case, the air inletting means includes, for example, the pressure-reduction bottle and a valve which enables selection of a state in which the tubular body is communicated with the atmosphere, and by switching the valve to cause the tubular body to be communicated with the atmosphere, air is inlet into a fluid channel between the valve and the pressure-reduction bottle. The air inletting means may be configured to inletting air into the fluid channel by a negative pressure by the pressure-reduction bottle.

The analysis apparatus of the present invention may further comprises control means for securing a space for filling the sample in the interior of the resistive body, for example, by causing the liquid to travel by the pressure-reduction pump after the interior of the resistive body is filled with the liquid to inletting air into the resistive body.

The control means is configured to, for example, after the liquid in the fluid channel is replaced with air, switch the valve to inlet the liquid in the fluid channel, and to stop the liquid in the fluid channel travelling when the flow rate sensor detects an interface between the liquid and the air. In this case, the volume of liquid inlet in the fluid channel is set to match or substantially match the volume of the space for filling the sample in the resistive body.

The control means may be configured to stop the air in the fluid channel travelling when the flow rate sensor detects the interface between the air inlet in the fluid channel and the liquid. In this case, the volume of the air inlet in the fluid channel is set to match or substantially match the volume of the space for filling the sample in the resistive body.

Preferably, the analysis apparatus of the present invention may further comprise a pressurizing pump which is provided at the halfway of a supply piping for inletting the liquid in the interior of the resistive body.

The sample is one containing grains, typically, a blood containing blood cells.

The resistive body has, for example, plural minute grooves through which the sample passes.

According to a second aspect of the present invention, there is provided an analysis method that comprises a first step of filling a liquid in an interior of a resistive body through which a sample passes, a second step of discharging some of the liquid filled in the interior of the resistive body, and of securing a space in the interior of the resistive body for filling the sample, a third step of supplying the sample into the space, a fourth step of causing the sample to travel in the interior of the resistive body, and a fifth step of measuring a travel time of the sample in the interior of the resistive body by using a flow rate sensor provided at a halfway of a discharging piping connected to the resistive body.

Preferably, in the analysis method of the present invention, as the flow rate sensor, a sensor including a tubular body and a sensor unit with a plurality of detecting areas for detecting an interface between the liquid and air travelling in the tubular body is used, and the analysis method further comprises a sixth step of inletting air into the tubular body, the sixth step being executed between the first step and the second step.

The first step is carried out by causing power by, for example, a pressure-reduction pump to act on a pressure-reduction bottle and the resistive body through the discharging piping. In this case, the sixth step is carried out by switching the valve provided at the halfway of the discharging piping, thereby letting the upstream side of the resistive body to be opened to the atmosphere.

The sixth step is carried out by causing a negative pressure of the pressure-reduction bottle to act on the piping with the pressure-reduction pump being terminated, for example. The sixth step is carried out by, for example, replacing, the fluid channel between the valve and the pressure-reduction bottle with air. In this case, the analysis method of the present invention may further comprise a seventh step of inletting the liquid into the fluid channel from the upstream of the valve by power by the pressure-reduction pump. The seventh step is carried out in such a manner as to stop the liquid in the fluid channel travelling when a flow rate sensor detects an interface between the liquid and the air and to ensure a space with a target volume in the interior of the resistive body.

The seventh step may be carried out by stopping the air in the fluid channel travelling when the flow rate sensor detects an interface between the air and the liquid inlet by the valve into the fluid channel between the valve and the pressure-reduction bottle.

Preferably, the pressure-reduction level when the fifth step is carried out is set to be smaller than that of the first step.

According to the analysis method of the present invention, as a sample, one containing grains, typically, a blood containing blood cells is used.

BRIEF DESCRIPTION OF DRAWINGS

FIG. 30A is a piping diagram for explaining a blood discharging operation from a blood filter in the blood inspecting apparatus shown in FIG. 28, and FIG. 30B is a cross-sectional view around the blood filter for explaining the blood discharging operation shown in FIG. 28;

DESCRIPTION FOR REFERENCE NUMERALS

1 Blood inspecting apparatus (analysis apparatus)
10 Control unit (control means)
2 Blood filter (resistive body)
33 Pressurizing pump
52 Three-way valve (valve)
53 Flow rate sensor
55 Pressure-reduction bottle
56 Pressure-reduction pump
58A to 58E Photosensor (detecting area) (of flow rate sensor)
59 Straight tube (tubular body) (of flow rate sensor)
71 to 73 (Supply) Piping
74 to 77 (Discharging) Piping
82 Space (for blood supply)
83 Isotonic sodium chloride solution (liquid)
85 Blood (sample)
Ar Air
In Interface

BEST MODE FOR CARRYING OUT THE INVENTION

A specific example will be given of a blood inspecting apparatus and a blood inspecting method of the present invention with reference to the accompanying drawings.

Figure 1:
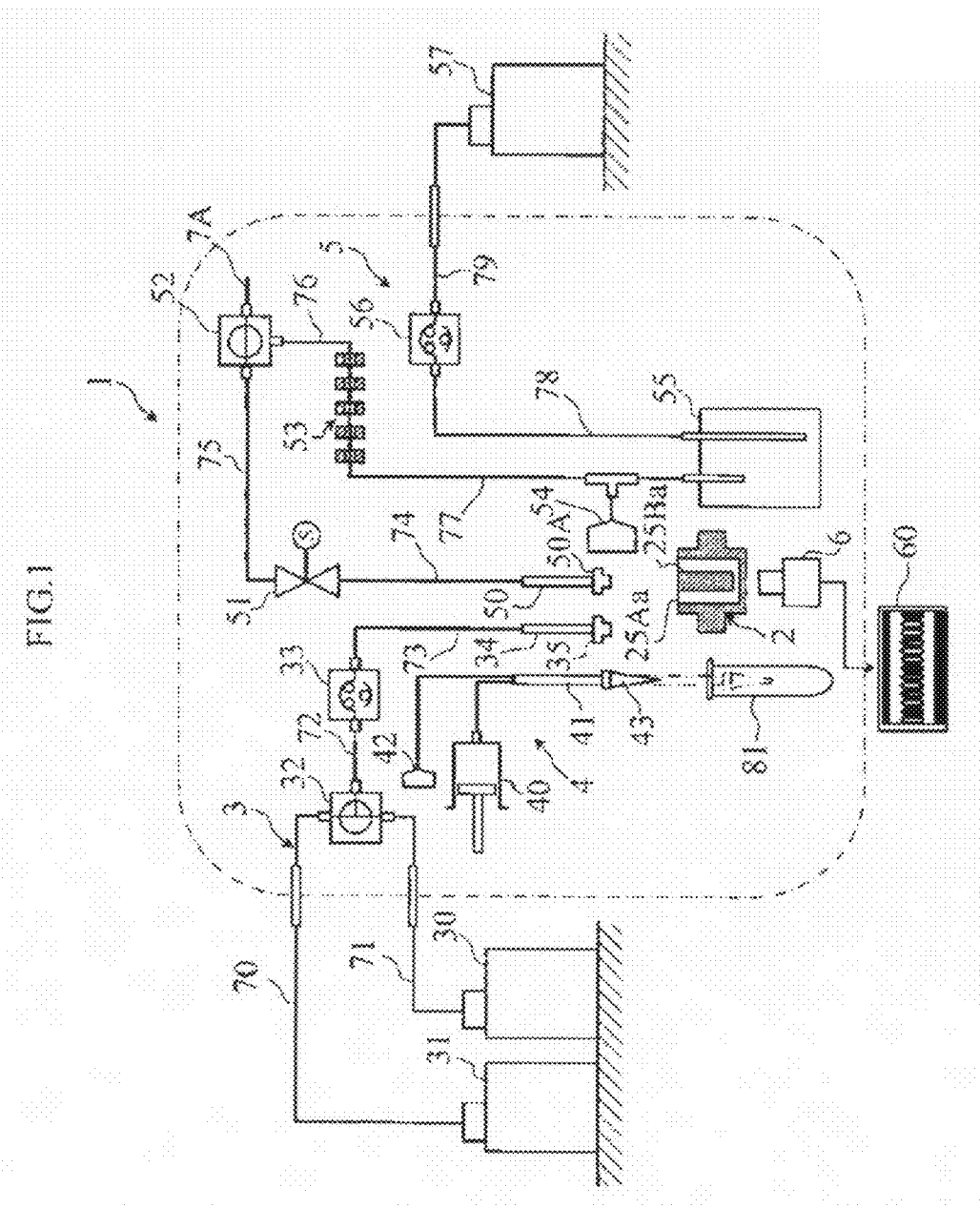
FIG. 1 is a piping diagram showing an illustrative blood inspecting apparatus according to the present invention.

A blood inspecting apparatus 1 shown in FIG. 1 is configured to, using a blood filter 2, measure a flowability of a blood sample like a whole blood, a transformation form of a red blood cell, an activity of a white blood cell, etc. The blood inspecting apparatus 1 includes a liquid supply mechanism 3, a sampling mechanism 4, a liquid discharging mechanism 5 and an imaging device 6.

As shown in FIGS. 2 to 5, the blood filter 2 regulates a fluid channel where a blood travels, and includes a holder 20, a fluid-channel substrate 21, a packing 22, a transparent cover 23, and a cap 24.

The holder 20 is for retaining the fluid-channel substrate 21, and enables supply of a liquid to the fluid-channel substrate 21 and discharging of a liquid from the fluid-channel substrate 21. The holder 20 has a pair of small-diameter cylinders 25A, 25B provided in the interiors of a rectangular tube 26 and a large-diameter cylinder 27. The pair of small-diameter cylinders 25A, 25B are formed in a cylindrical shape having respective upper openings 25Aa, 25Ba, and respective lower openings 25Ab, 25Bb, and are integrated together with the rectangular tube 26 and the large-diameter cylinder 27 by fins 25C. The large-diameter cylinder 27 is for fixing the fluid-channel substrate 21, and has a cylindrical recess 27A. The cylindrical recess 27A is a part where the packing 22 is fitted, and a pair of cylindrical convexities 27Aa are formed in the interior of the recess. Provided between the rectangular tube 26 and the large-diameter cylinder 27 is a flange 20A. The flange 20A is used to fix the cap 24 to the holder 20, and is formed in a substantially rectangular shape as viewed from the above. Cylindrical protrusions 20C are provided at respective corners 20B of the flange 20A.

Figure 3:
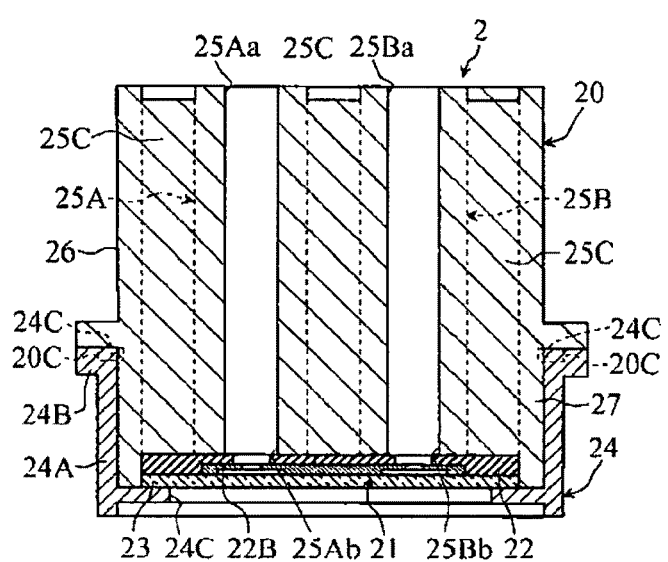
FIG. 3 is a cross-sectional view along a line III-III in FIG. 2.
Figure 4:
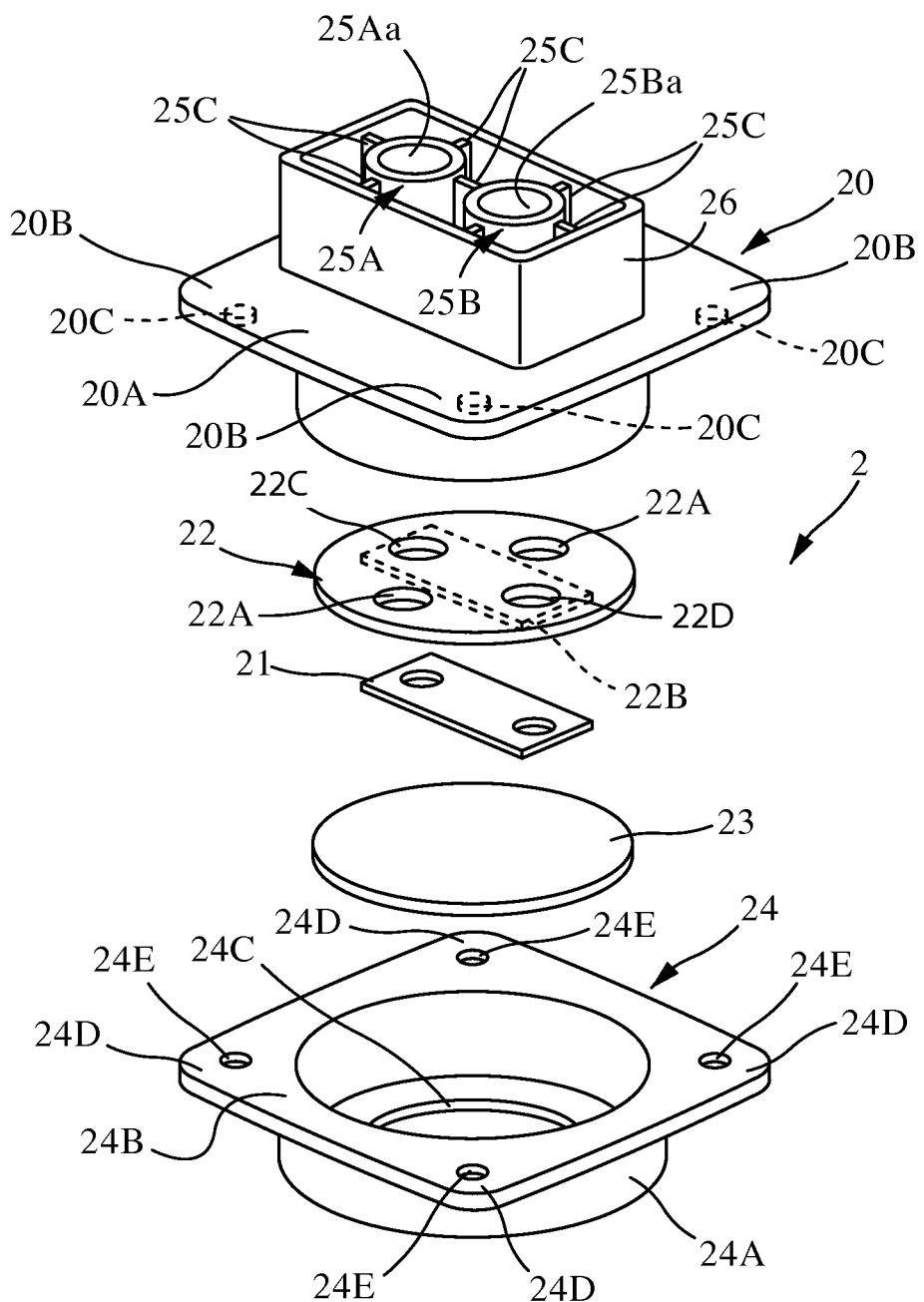
FIG. 4 is an exploded perspective view of the blood filter shown in FIG. 2.
Figure 5:
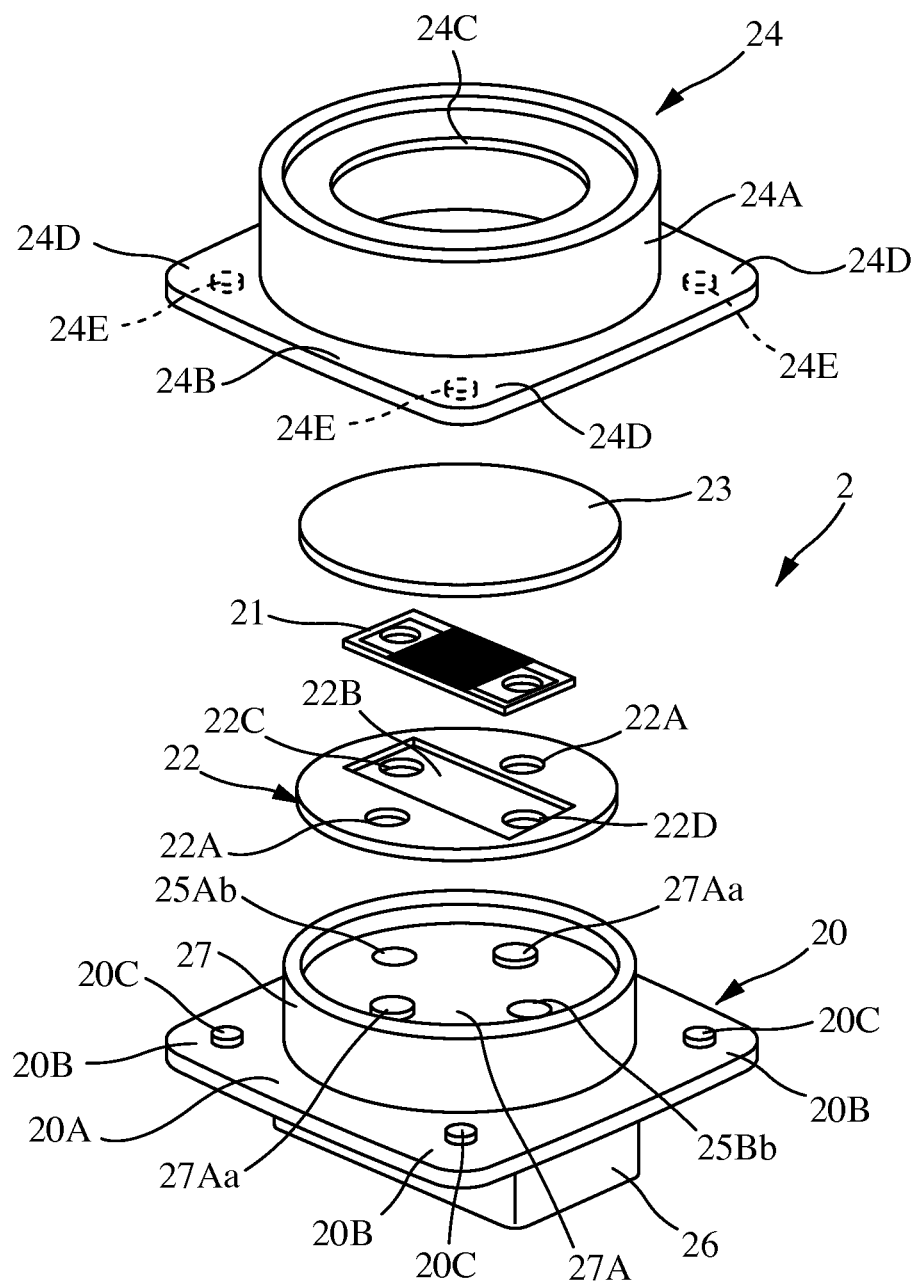
FIG. 5 is an exploded perspective view showing the blood filter as viewed from a bottom.
Figure 6A:
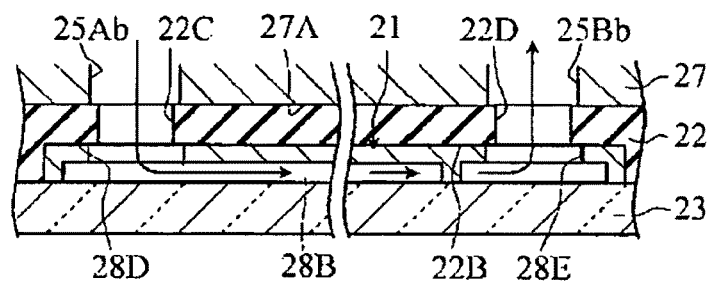
FIGS. 6A to 6C are cross-sectional views showing a major part for explaining the blood filter shown in FIG. 2.
Figure 6B:
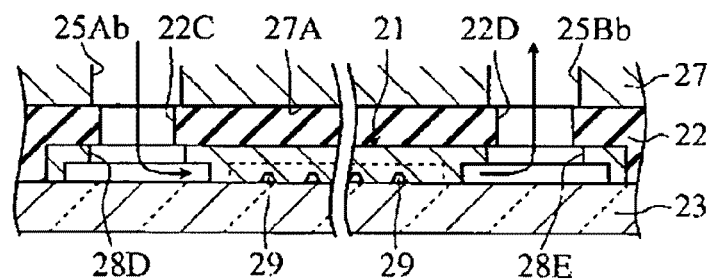
Figure 6C:
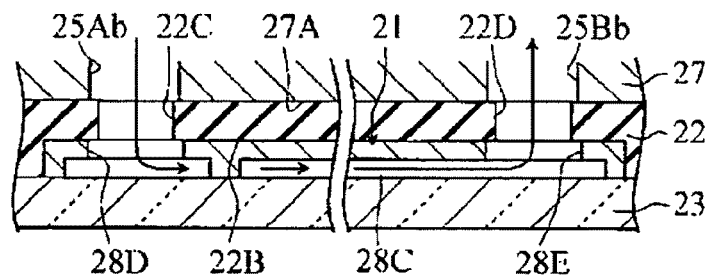
Figure 7:
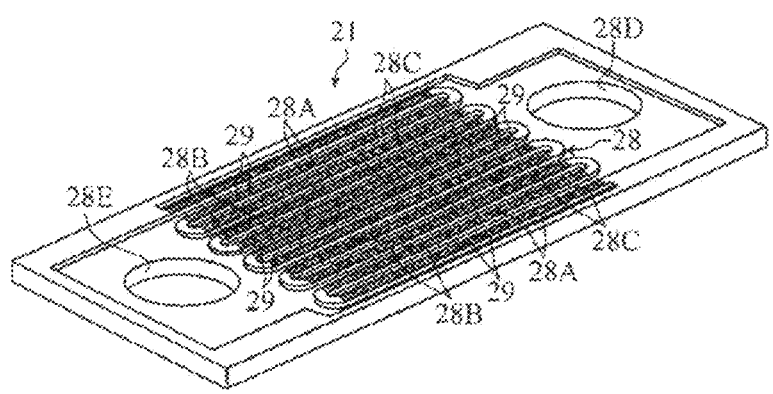
FIG. 7 is an overall perspective view of a fluid-channel substrate in the blood filter shown in FIG. 2.
Figure 8A:
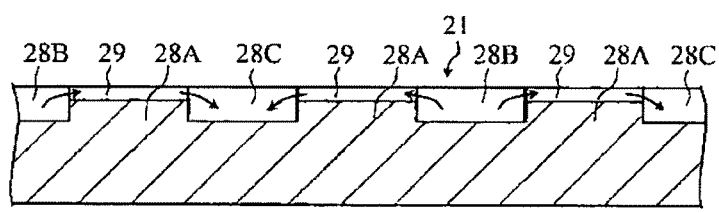
FIG. 8A is a cross-sectional view showing a major part of a cross section along a communicating groove in the fluid-channel substrate shown in FIG. 7.
Figure 8B:
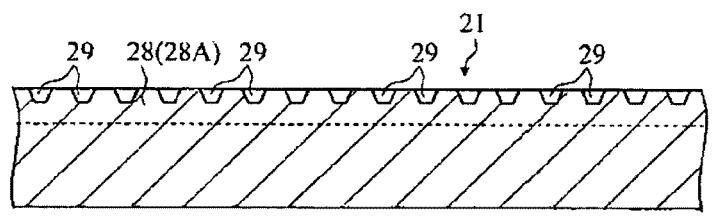
FIG. 8B is a cross-sectional view showing a major part of a cross section along the straight part of a bank in the fluid-channel substrate shown in FIG. 7.
Figure 9:
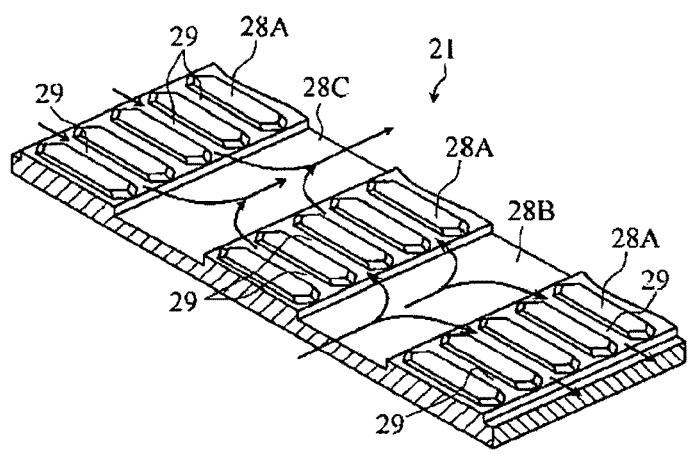
FIG. 9 is a perspective view showing a major part of the fluid-channel substrate shown in FIG. 7 enlarged.

As shown in FIGS. 3 and 6, the fluid-channel substrate 21 gives a travel resistance when a blood travels, functions as a filter, and is fixed to the large-diameter cylinder 27 (cylindrical recess 27A) of the holder 20 via the packing 22. As shown in FIGS. 7 to 9, the fluid-channel substrate 21 is formed of, for example, a silicon in a rectangular tabular shape as a whole, and has a bank 28 and plural communicating grooves 29 formed by applying a photolithography technique or by performing an etching process on one surface of the tabular silicon.

The bank 28 is so formed as to serpentine at the center of the fluid-channel substrate 21 in the lengthwise direction. The bank 28 has plural straight portions 28A running in the lengthwise direction of the fluid-channel substrate 21, and an inlet fluid channel 28B and a discharging fluid channel 28C are defined by those straight portions 28A. Through holes 28D, 28E corresponding to respective lower openings 25Ab, 25Bb of the small-diameter cylinders 25A, 25B of the holder 20 are formed at both sides of the bank 28 as shown in FIGS. 6 and 7. The through hole 28D is for inletting a liquid from the small-diameter cylinder 25A to the fluid-channel substrate 21, and the through hole 28E is for discharging a liquid in the fluid-channel substrate 21 to the small-diameter cylinder 25B.

On the other hand, as shown in FIGS. 6 to 9, the plural communicating grooves 29 are so formed as to extend in the widthwise direction of the bank 28 at the straight portions 28A thereof. That is, the communicating grooves 29 cause the inlet fluid channel 28B to be communicated with the discharging fluid channel 28C. When a transformability of a cell like a blood cell or a blood platelet is observed, each communicating groove 29 is set to have a width dimension smaller than the diameter of a cell, and is set to be, for example, 4 to 6 μm. Moreover, a space between adjoining communicating grooves 29 is set to be, for example, 15 to 20 μm.

According to the fluid-channel substrate 21, a liquid introduced through the through hole 28D successively travels the inlet fluid channel 28B, the communicating grooves 29, and the discharging fluid channel 28C, and is discharged from the fluid-channel substrate 21 through the through hole 28E.

As shown in FIGS. 2 to 6, the packing 22 is for retaining the fluid-channel substrate 21 in the large-diameter cylinder 27 of the holder 20 in a liquid-tight manner. The packing 22 is formed in a discoid shape as a whole, and is fitted into the cylindrical recess 27A of the large-diameter cylinder 27 of the holder 20. The packing 22 is provided with a pair of through holes 22A and a rectangular recess 22B. The pair of through holes 22A are portions where respective cylindrical convexities 27A of the large-diameter cylinder 27 of the holder 20 are fitted. As respective cylindrical convexities 27Aa are fitted in the pair of through holes 22A, the packing 22 is positioned relative to the large-diameter cylinder 27. The rectangular recess 22B is for retaining the fluid-channel substrate 21, and is formed in a shape corresponding to the contour of the fluid-channel substrate 21. However, the depth of the rectangular recess 22B is set to be substantially same as the maximum thickness of the fluid-channel substrate 21 or slightly smaller than that. The rectangular recess 22B is provided with a pair of communicating holes 22C, 22D. Those communicating holes 22C, 22D are for causing respective lower openings 25Ab, 25Bb of the small-diameter cylinders 25A, 25B of the holder 20 to be communicated with the through holes 28D, 28E of the fluid-channel substrate 21.

As shown in FIGS. 3 to 6, the transparent cover 23 abuts the fluid-channel substrate 21 to cause the inlet fluid channel 28B, the communicating grooves 29, and the discharging fluid channel 28C of the fluid-channel substrate 21 to have a closed cross-sectional structure. The transparent cover 23 is formed of, for example, a glass in a discoid shape. The transparent cover 23 has a thickness set to be smaller than the depth of the cylindrical recess 27A of the large-diameter cylinder 27 of the holder 20, and the total of the maximum thicknesses of the transparent cover 23 and the packing 22 is set to be larger than the depth of the cylindrical recess 27A.

As shown in FIGS. 2 to 5, the cap 24 is for fixing the fluid-channel substrate 21 together with the packing 22 and the transparent cover 23, and has a cylinder 24A and a flange 24B. The cylinder 24A overcoats the large-diameter cylinder 27 of the holder 20, and has a through hole 24C. The through hole 24C is for ensuring the visibility when a travel condition of a blood in the fluid-channel substrate 21 is checked. The flange 24B has a form corresponding to the flange 20A of the holder 20, and has recesses 24E at respective corners 24D. The recess 24E is a part where the cylindrical protrusion 20C of the flange 20A of the holder 20 is fitted.

As explained above, the transparent cover 23 has a thickness which is set to be smaller than the depth of the cylindrical recess 27A in the large-diameter cylinder 27 of the holder 20, and the total of the maximum thicknesses of the transparent cover 23 and the packing 22 is set to be larger than the depth of the cylindrical recess 27A. On the other hand, the rectangular recess 22B has a depth set to be substantially same or slightly larger than the maximum thickness of the fluid-channel substrate 21. Accordingly, when the fluid-channel substrate 21 is fixed together with the packing 22 and the transparent cover 23 by the cap 24, the packing 22 is compressed and the transparent cover 23 liquid-tightly contacts the fluid-channel substrate 21 appropriately, so that it is possible to prevent any leakage of a liquid between the fluid-channel substrate 21 and the transparent cover 23.

The liquid supply mechanism 3 shown in FIG. 1 is for supplying a liquid to the blood filter 2, and includes bottles 30, 31, a three-way valve 32, a pressurizing pump 33, and a liquid supply nozzle 34.

The bottles 30, 31 are for reserving a liquid to be supplied to the blood filter 2. The bottle 30 reserves an isotonic sodium chloride solution used for inspection of a blood, and is connected to the three-way valve 32 by a piping 71. On the other hand, the bottle 31 is for retaining a distilled water for rinsing of the piping, and is connected to the three-way valve 32 by a piping 70.

The three-way valve 32 is for selecting a kind of a liquid to be supplied to the liquid supply nozzle 34, and is connected to the pressurizing pump 33 by a piping 72. That is, by switching the three-way valve 32 as needed, either one of the states: a state in which the isotonic sodium chloride solution is supplied to the liquid supply nozzle 34 from the bottle 30; and a state in which the distilled water is supplied to the liquid supply nozzle 34 from the bottle 31 can be selected.

The pressurizing pump 33 provides power for moving a liquid from the bottles 30, 31 to the liquid supply nozzle 34, and is connected to the liquid supply nozzle 34 by a piping 73. Various kinds of conventionally known pumps can be used as the pressurizing pump 33, but from the standpoint of miniaturization of the apparatus, it is preferable to use a tube pump.

The liquid supply nozzle 34 is for supplying a liquid from each bottle 30, 31 to the blood filter 2, and is attached to the upper opening 25Aa (see FIGS. 2 and 3) of the small-diameter cylinder 25A of the blood filter 2. The liquid supply nozzle 34 has a joint 35 which is attached to the upper opening 25Aa (see FIGS. 2 and 3), and has another end connected to the pressurizing pump 33 by a piping 73.

The sampling mechanism 4 is for supplying a blood to the blood filter 2, and includes a sampling pump 40, a blood supply nozzle 41, and a liquid-level detecting sensor 42.

The sampling pump 40 is for providing power for suctioning/delivering a blood, and comprises, for example, a syringe pump.

The blood supply nozzle 41 is used with a chip 43 being attached to a leading end thereof, and suctions a blood into the interior of the chip 43 from a blood collecting tube 81 as the sampling pump 40 applies a negative pressure to the interior of the chip 43, and delivers the blood as the sampling pump 40 pressurizes the blood in the chip.

The liquid-level sensor 42 is for detecting the liquid level of the blood suctioned into the interior of the chip 43. When the pressure inside the chip 43 becomes a predetermined value, the liquid-level sensor 42 outputs a signal to that effect, and detects that a target amount of blood is suctioned.

The liquid discharging mechanism 5 is for discharging a liquid inside each piping and the blood filter 2, and includes a liquid discharging nozzle 50, an electromagnetic valve 51, a three-way valve 52, a flow rate sensor 53, a pressure sensor 54, a pressure-reduction bottle 55, a pressure-reduction pump 56, and a liquid discharging bottle 57.

The liquid discharging nozzle 50 is for suctioning a liquid inside the blood filter 2, and is attached to the upper opening 25Ba (see FIGS. 2 and 3) of the small-diameter cylinder 25B in the blood filter 2. The liquid discharging nozzle 50 has a joint 50A which is provided at a leading end thereof and attached to the upper opening 25Ba of the blood filter 2, and has another end connected to the electromagnetic valve 51 by a piping 74.

The electromagnetic valve 51 is for selecting a communicating state between the liquid discharging nozzle 50 and the three-way valve 52, and for selecting a state in which a waste liquid is supplied from the liquid discharging nozzle 57 to the three-way valve 52 and a state in which such a waste liquid is not supplied thereto. The electromagnetic valve 51 is connected to the three-way valve 52 by a piping 75. Needless to say, various kinds of valves like an electric valve can be used instead of the electromagnetic valve 51.

The three-way valve 52 is connected to the flow rate sensor 53 by a piping 76, and a piping 7A to be opened to the atmosphere is connected thereto. The three-way valve 52 can select a state in which a liquid is discharged to the pressure-reduction bottle 55 and a state in which air is inlet to a piping 76 through the piping 7A.

Figure 10:
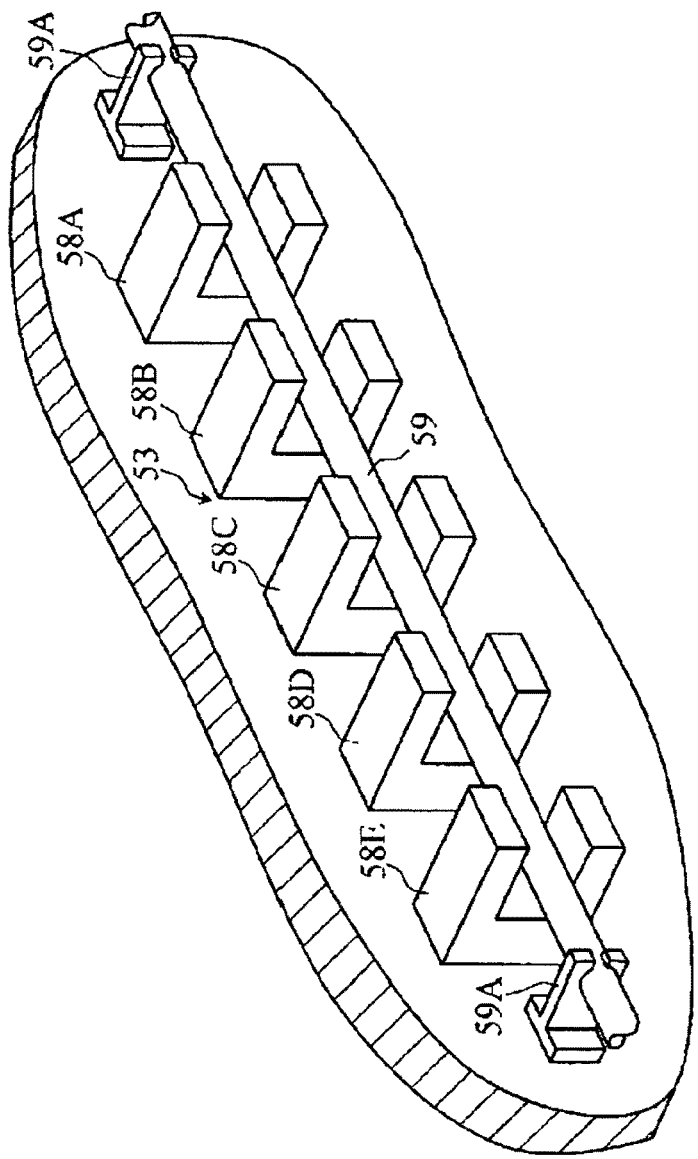
FIG. 10 is a perspective view showing a flow rate sensor in the blood inspecting apparatus shown in FIG. 1.
Figure 11:
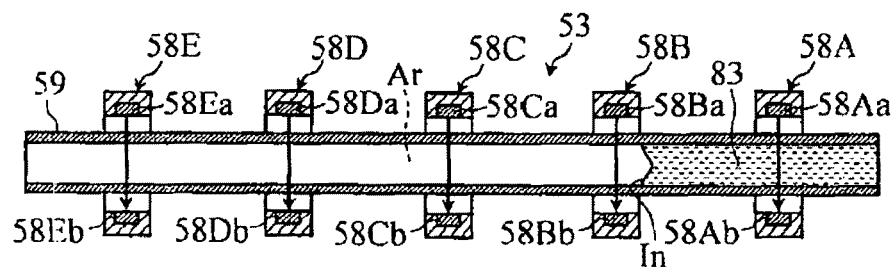
FIG. 11 is a cross-sectional view for explaining how the flow rate sensor shown in FIG. 10 works.

As shown in FIGS. 10 and 11, the flow rate sensor 53 tracks a position of an interface In between an air Ar and an isotonic sodium chloride solution 83 to measure a travel time of a blood, and includes plural (in the figures, five) photo sensors 58A, 58B, 58C, 58D, and 58E and a straight tube 59.

The plural photo sensors 58A to 58E are for detecting whether or not the interface In between the air Ar and the isotonic sodium chloride solution 83 reaches (passes through) a corresponding predetermined area in the straight tube 59, and are arranged side by side in a horizontal direction with an equal clearance. Each photo sensor 58A to 58E comprises a light emitting device 58Aa, 58Ba, 58Ca, 58Da, 58Ea and a photo sensitive device 58Ab, 58Bb, 58Cb, 58Db, and 58Eb, and the flow rate sensor is configured as a transmissive sensor having those devices 58Aa to 58Ea, 58Ab to 58Eb arranged so as to face with each other.

Needless to say, the photo sensors 58A to 58E are not limited to a transmissive type, but a reflective type can be used.

The straight tube 59 is a part where the interface In between the air Ar and the isotonic sodium chloride solution 83 moves at the time of inspection, is connected to the three-way valve 52 by the piping 76, and is communicated with the interior of the pressure-reduction bottle 55 by a piping 77 (see FIG. 1). It is preferable that the internal diameter in the vicinity of the straight tube 59 in the pipings 76, 77 is set to be same or substantially same (e.g., −3% to +3% of the internal area of the straight tube 59) as that of the straight tube 59. The straight tube 59 is arranged so as to run in the horizontal direction and to be arranged between the light emitting devices 58Aa to 58Ea and the photo sensitive devices 58Ab to 58Eb by a support 59A. The straight tube 59 is formed of a material with a translucency, e.g., a transparent glass or a transparent resin in a cylindrical shape having a uniform cross section. A cylinder with a uniform cross section means a circular cross section with a constant or substantially constant internal diameter (e.g., an internal diameter within a range from −3% to +3% with respect to a target internal area). It is appropriate if the internal diameter of the straight tube 59 is set to be within a range where a travel time of the interface In between the air Ar and the isotonic sodium chloride solution 83 can be appropriately measured, and for example, is set to be 0.5 mm to 3 mm. When a part where the air Ar moves, e.g., the internal diameter of the straight tube 59 is set to be uniform (constant or substantially constant), or when, in addition to the straight tube 59, the internal diameter in the vicinity of the straight tube 59 in the pipings 76, 77 connected to the straight tube 56 is set to be same or substantially same as that of the straight tube 59, even if the air Ar moves back and forth in the straight tube 59, it is possible to prevent any change in a contact area between the air Ar and the internal surface of the piping, thereby maintaining the contact area constant or substantially constant. Moreover, when a dimensional error of the internal diameter is taken into consideration, it is desirable that the straight tube 59 should be formed of a transparent glass. This enables precise measurement of a travel time of the interface In.

Figure 12:
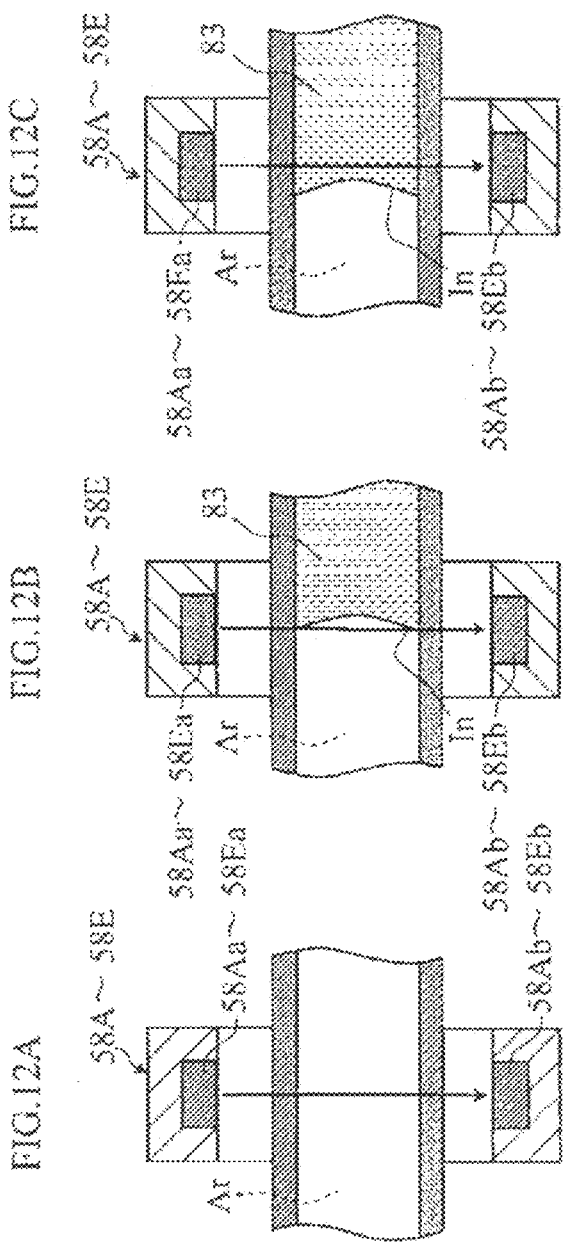
FIG. 12 (FIGS. 12A-12C) is/are a cross-sectional view(s) showing a major part of the flow rate sensor shown in FIG. 10 enlarged in order to explain how it works.
Figure 13:
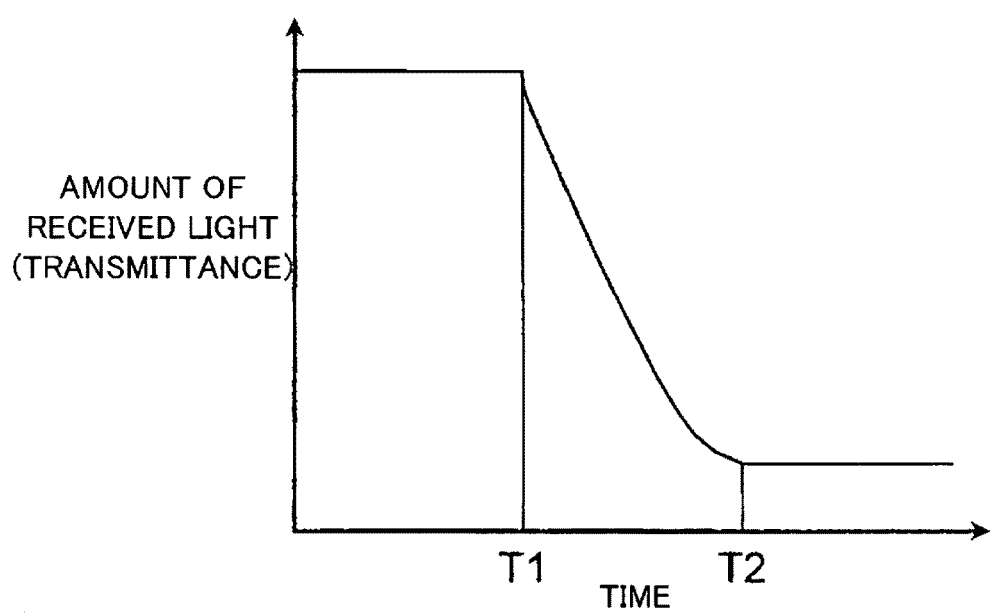
FIG. 13 is a graph showing illustrative optical information obtained by each photo sensor in the flow rate sensor shown in FIG. 10.

As shown in FIGS. 12A and 12B, when the interface In between the air Ar and the isotonic sodium chloride solution 83 moves in the straight tube 59, because a ratio between the air Ar and the isotonic sodium chloride solution 83 at an area corresponding to each photosensor 58A to 58E gradually changes, as shown in FIG. 13, the amount of received light (transmittance) obtained by the photo sensitive devices 58Ab to 58Eb of the photo sensors 58A to 58E changes. Accordingly, with reference to a time T1 when the amount of received light (transmittance) obtained by the photo sensors 58A to 58E starts changing, or a time T2 when the amount of received light (transmittance) becomes constant after it starts changing, it is possible to detect that the interface In (the isotonic sodium chloride solution 83) between the air Ar and the isotonic sodium chloride solution 83 reaches at the photo sensors 58A to 58E. When individual photo sensors 58A to 58E detect that the interface In (the isotonic sodium chloride solution 83) between the air Ar and the isotonic sodium chloride solution 83 reaches thereto, it is possible to detect a time when the interface In between the air Ar and the isotonic sodium chloride solution 83 passes through between adjoining photo sensors 58A to 58E, i.e., a travel time of the isotonic sodium chloride solution 83. Moreover, by providing equal to or greater than three photo sensors 58A to 58E, it is possible to measure not only a travel time of the isotonic sodium chloride solution 83 at a certain time but also a change in the travel time of the isotonic sodium chloride solution 83 along with advancement of time. Note that an arrangement clearance of the plural photo sensors 58A to 58E is selected from a distance corresponding to 10 to 30 μL with reference to a flow rate.

Figure 2:
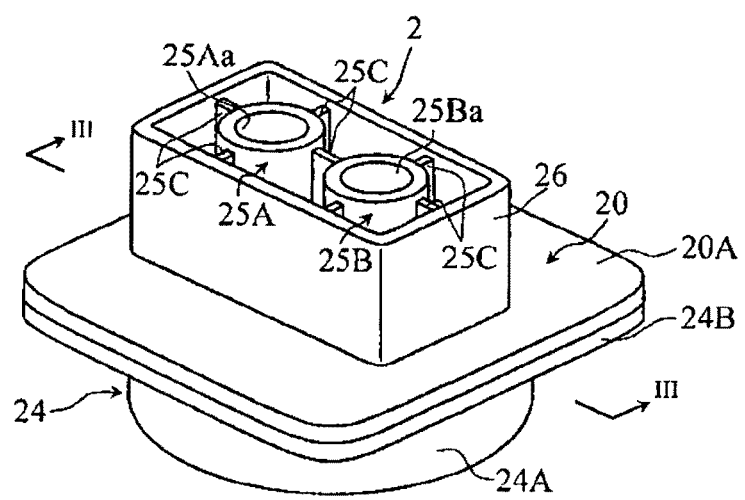
FIG. 2 is an overall perspective view for explaining a blood filter used in the blood inspecting apparatus shown in FIG. 1.

The travel time of the isotonic sodium chloride solution 83 depends on a travel resistance when a blood travels through the fluid-channel substrate 21 in the blood filter 2 (see FIGS. 1 to 3). Accordingly, detecting of the travel time of the isotonic sodium chloride solution 83 by the flow rate sensor 53 enables acquisition of information on the flowability or the like of the blood.

The pressure sensor 54 shown in FIG. 1 is for monitoring a pressure of a liquid traveling through the piping 77, and is provided at the halfway of the piping 77. A monitoring result of the pressure by the pressure sensor 54 is subjected to feedback to the pressure-reduction pump 56 to be discussed later, so that the pressure of a liquid flowing through the piping 77 and thus a liquid in the interior of the blood filter 2 is maintained substantially at constant. The pressure of the liquid in the interior of the blood filter 2 can be maintained substantially at constant by monitoring the pressure level in the pressure-reduction bottle 55 instead of providing the pressure sensor 54.

The pressure-reduction bottle 55 is for temporarily reserving a waste liquid, and is for defining a pressure-reduction space. The pressure-reduction bottle 55 is connected to the pressure-reduction pump 56 by a piping 78.

The pressure-reduction pump 56 is for reducing the pressure inside the pressure-reduction bottle 55 in order to suction a liquid inside the blood filter 2 or to inlet the air Ar (see FIG. 11) into the piping 76. The pressure-reduction pump 56 is connected to the liquid discharging bottle 57 by a piping 79, and also has a function of feeding a waste liquid in the pressure-reduction bottle 55 to the liquid discharging bottle 57. Various kinds of pumps can be used as the pressure-reduction pump 56, but from the standpoint of miniaturization of the apparatus, it is preferable to use a tube pump.

The liquid discharging bottle 57 is for reserving a waste liquid inside the blood filter 2 and the pipings 74 to 77 when a blood is inspected or a waste liquid when the pipings 72 to 77 are rinsed.

The imaging device 6 is for picking up an image of a travel state of a blood in the fluid-channel substrate 21. The imaging device 6 comprises, for example, a CCD camera, and is arranged so as to position ahead of the fluid-channel substrate 21. An imaging result by the imaging device 6 is output to, for example, a monitor 60, so that it is possible to check the travel state of the blood in real time or as a recorded image.

Figure 14:
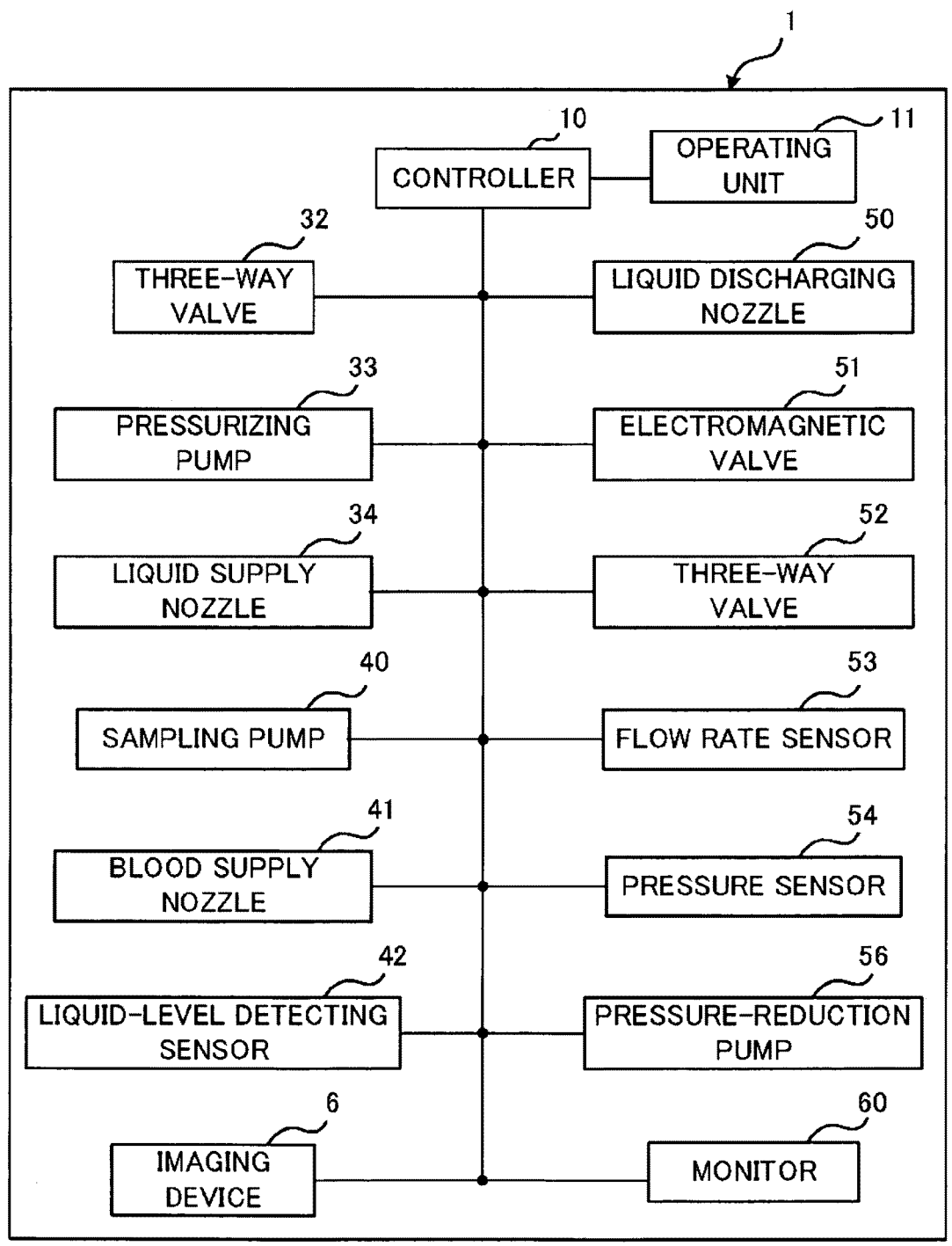
FIG. 14 is a block diagram of the blood inspecting apparatus shown in FIG. 1.

The blood inspecting apparatus 1 further includes a controller 10 and an operating unit 11 as shown in FIG. 14 in addition to the individual units shown in FIG. 1.

The controller 10 is for controlling individual units. The controller 10 performs, for example, switching control on the three-way valves 32, 52, opening/closing control on the electromagnetic valve 51, driving control on each pump 33, 40, and 56, driving control on each nozzle 34, 41, and 50, and operation control on the imaging device 6 and the monitor 60.

The operating unit 11 performs arithmetic operation necessary for causing individual units to operate, e.g., calculates a control level for each pump 33, 40, and 56 based on a monitoring result by the liquid-level detecting sensor 42 and the pressure sensor 54, and performs arithmetic operation necessary for the opening/closing control of the electromagnetic valve 51 and for the switching control of the three-way valve 52 based on a monitoring result by the flow rate sensor 53. The operating unit 11 further calculates a travel time (flowability) of a blood in the blood filter 2 based on a monitoring result by the flow rate sensor 53.

Next, an explanation will be given of an operation of the blood inspecting apparatus 1.

Figure 15:
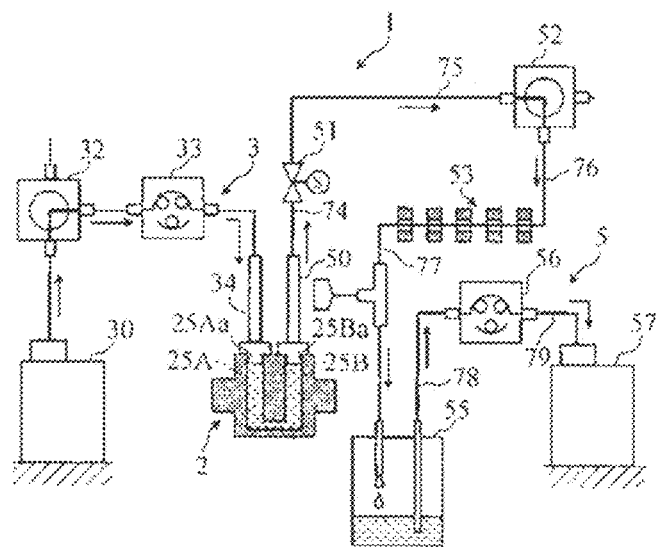
FIG. 15 is a piping diagram for explaining a gas/liquid replacement operation by the blood inspecting apparatus shown in FIG. 1.

First, as shown in FIG. 15, with the blood filter 2 being set at a predetermined position, an initiation of starting measurement is given. This initiation is, for example, automatically given as a user operates a button of the blood inspecting apparatus 1 or is automatically given as the user sets the blood filter 2 thereto. When recognizing that the initiation of starting measurement is given, the controller 10 (see FIG. 14) performs a gas/liquid replacement operation in the interior of the blood filter 2. More specifically, first, the controller 10 (see FIG. 14) attaches the liquid supply nozzle 34 of the liquid supply mechanism 3 to the upper opening 25Aa of the small-diameter cylinder 25A in the blood filter 2, and attaches the liquid discharging nozzle 50 of the liquid discharging mechanism 5 to the upper opening 25Ba of the small-diameter cylinder 25B in the blood filter 2. On the other hand, the controller 10 (see FIG. 14) switches the three-way valve 32 to make the bottle 30 communicated with the liquid supply nozzle 34, and switches the three-way valve 52 and opens the electromagnetic valve 51 to make the liquid discharging nozzle 50 communicated with the pressure-reduction bottle 55. That is, the path between the bottle 30 and the pressure-reduction bottle 55 is communicated through the interior of the blood filter 2. In this state, the controller 10 (see FIG. 14) actuates the pressurizing pump 33 of the liquid supply mechanism 3 and the pressure-reduction pump 56 of the liquid discharging mechanism 5. The pressure by the pressurizing pump 33 is set to be, for example, 1 to 150 kPa, and the reduced pressure by the pressure-reduction pump 56 is set to be 0 to −50 kPa.

When the pressurizing pump 33 and the pressure-reduction pump 56 are actuated in this fashion, an isotonic sodium chloride solution in the liquid bottle 30 is supplied to the liquid supply nozzle 34 through the pipings 71 to 73, passes through the interior of the blood filter 2, and is discharged in the pressure-reduction bottle 55 through the liquid discharging nozzle 50 and the pipings 74 to 77. The isotonic sodium chloride solution discharged in the pressure-reduction bottle 55 is discharged in the liquid discharging bottle 57 through the pipings 78, 79 by power of the pressure-reduction pump 56. Accordingly, a gas in the interior of the blood filter 2 is evacuated by the isotonic sodium chloride solution, and the interior of the blood filter 2 is replaced with the isotonic sodium chloride solution.

According to the blood inspecting apparatus 1, the gas/liquid replacement for the blood filter 2 is carried out by using the pressurizing pump 33 arranged at the upstream side of the blood filter 2 and the pressure-reduction pump 56 arranged at the downstream side of the blood filter 2. Accordingly, in comparison with a case in which the pressure-reduction pump 56 arranged at the downstream side of the blood filter 2 is used, a possibility that air bubbles remain in the interior of the blood filter 2 is remarkably reduced, and a time necessary for evacuating the gas in the interior of the blood filter 2 can be also reduced. This enables reduction of a time necessary for a blood inspection. Moreover, according to the blood inspecting apparatus 1, although the pressurizing pump 33 is also used together with the pressure-reduction pump 56, pump power necessary for a gas/liquid replacement is reduced and a replacement time can be shortened, thereby reducing the running cost.

Figure 16:
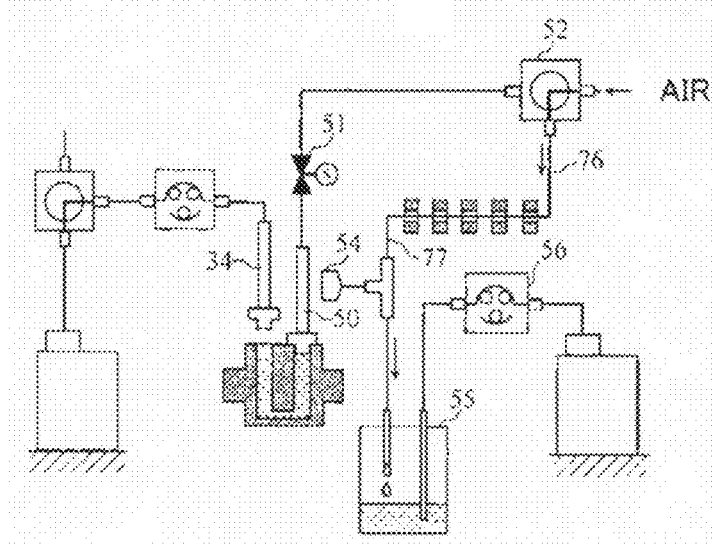
FIG. 16 is a piping diagram for explaining an air inletting operation by the blood inspecting apparatus shown in FIG. 1.
Figure 17:
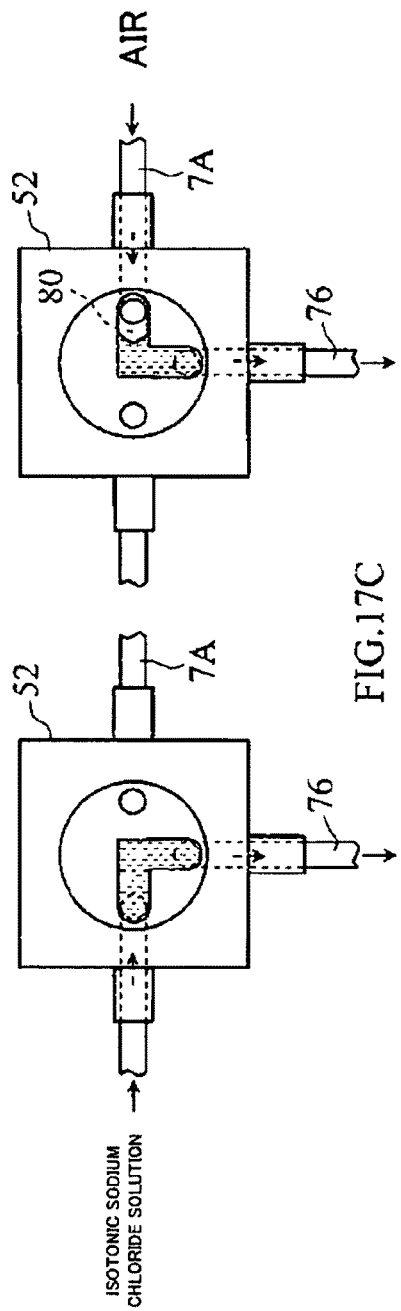
FIGS. 17A to 17C are partial transparent views for explaining the states around a three-way valve in the air inletting operation by the blood inspecting apparatus shown in FIG. 1.

Next, in the blood inspecting apparatus 1, as shown in FIG. 16, a process of inletting an air into the interior of the piping 76 is executed. More specifically, the controller 10 (see FIG. 14) closes the electromagnetic valve 51 and terminates operation of the pressure-reduction pump 56, and switches the three-way valve 52 into a state shown in FIG. 17B from a state shown in FIG. 17A, to make the piping 76 communicated with the atmosphere by the piping 7A. On the other hand, the controller 10 (see FIG. 14) actuates the pressure-reduction pump 56. Accordingly, the piping 7A and the piping 76 are subjected to pressure reduction, as shown in FIGS. 17B and 17C, the air Ar is inlet into the piping 76 through the piping 7A. Inletting of the air Ar into the piping 76 is carried out until the interior of the piping 76 is completely replaced with the air Ar. Replacement with the air Ar is carried out by letting the piping 86 to be opened to the atmosphere for a preset time and by switching the three-way valve 52, or by monitoring the internal pressure of the piping 76 by the pressure sensor 54 and by switching the three-way valve 52 when the internal pressure of the piping 76 becomes a predetermined value. Needless to say, inletting of the air Ar into the piping 76 can be carried out by a residual pressure of the pressure-reduction bottle 55 (see FIG. 16) without actuating the pressure-reduction pump 56.

Figure 18:
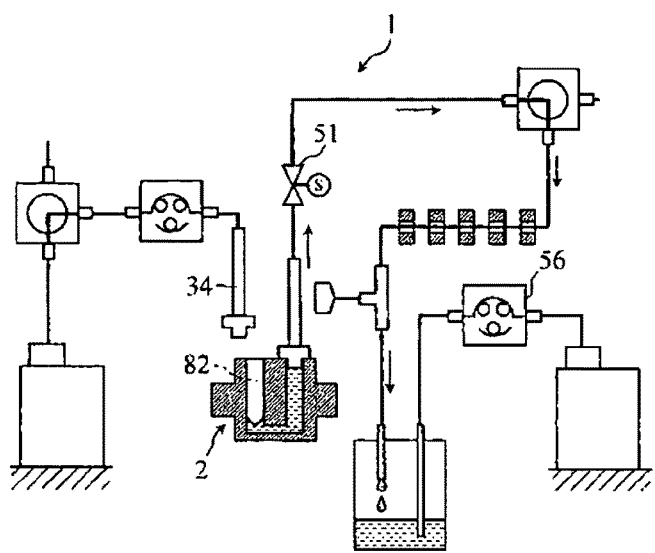
FIG. 18 is a piping diagram for explaining a liquid discharging operation for forming a space in the blood filter in the blood inspecting apparatus shown in FIG. 1.
Figure 19A:
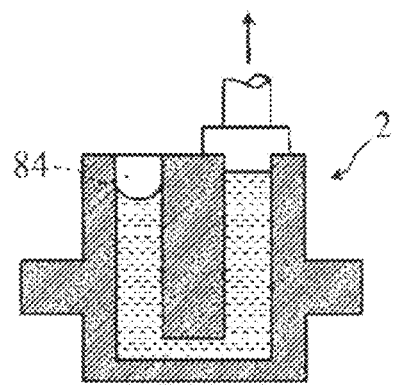
FIGS. 19A and 19B are cross-sectional views around the blood filter in the liquid discharging operation.
Figure 19B:
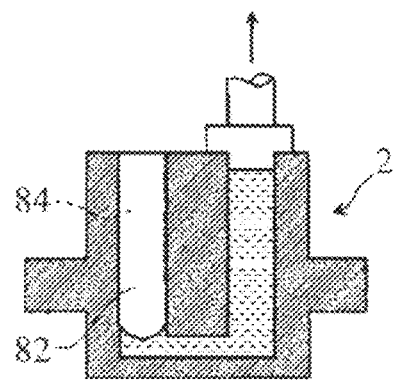
Figure 20A:
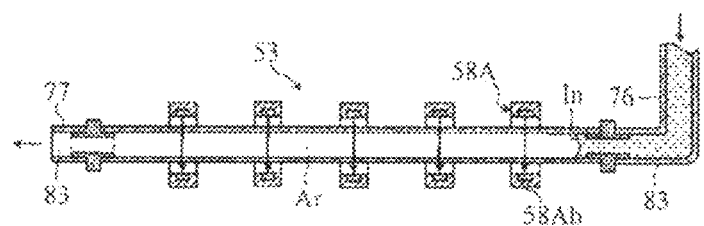
FIGS. 20A and 20B are cross-sectional views for explaining states around the flow rate sensor in the liquid discharging operation.
Figure 20B:
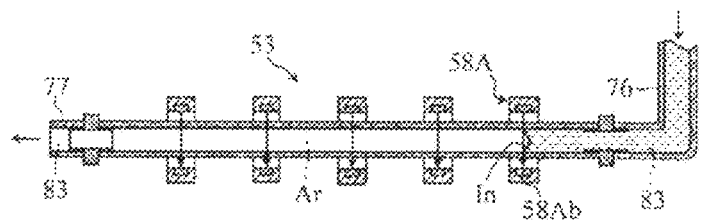

Next, as shown in FIG. 18, according to the blood inspecting apparatus 1, a predetermined amount of isotonic sodium chloride solution is discharged from the blood filter 2, and a space 82 necessary for supplying a blood to the blood filter 2 is secured. More specifically, the controller 10 (see FIG. 14) opens the electromagnetic valve 51 with the liquid supply nozzle 34 being detached from the blood filter 2. At this time, the pressure-reduction bottle 55 (see FIG. 16) is in a pressure-reduction state by the air replacement for the piping 76 carried out previously. Accordingly, as the electromagnetic valve 51 is opened, as shown in FIGS. 19A and 19B, the isotonic sodium chloride solution in the interior of the blood filter 2 is suctioned and eliminated through the liquid discharging nozzle 50, and air 84 is inlet in the blood filter 2. At this time, as shown in FIGS. 20A and 20B, the isotonic sodium chloride solution 83 in the pipings 76, 77 is moved toward the pressure-reduction bottle 55 (see FIG. 18), and together with this, the air Ar in the piping 76 is moved toward the pressure-reduction bottle 55 (see FIG. 18).

On the other hand, the photo sensor 58A of the flow rate sensor 53 detects whether or not the interface In between the isotonic sodium chloride solution 83 and the air Ar reaches thereto. As explained above, when the interface In passes through the photo sensor 58A, the amount of received light by the photo sensitive device 58Ab becomes small, and thus the photo sensor 58A can detect that the interface In reaches thereto. When the photo sensor 58A detects that the interface In reaches thereto, the controller 10 (see FIG. 14) closes the electromagnetic valve 51 (see FIG. 18) to prevent the isotonic sodium chloride solution 83 and the interface In from travelling.

The amount of isotonic sodium chloride solution 83 introduced in the piping 76 until the interface In is detected by the photo sensor 58A (the amount of discharged isotonic sodium chloride solution from the blood filter 2) is same or substantially same as the amount of blood to be supplied to the blood filter 2. That is, the volume of the piping 76 at the upstream side from the photo sensor 58A is set in accordance with the amount of blood to be supplied to the blood filter 2. Accordingly, by closing the electromagnetic valve 51 (see FIG. 18) when the interface In is detected by the photo sensor 58A, the space 82 with a volume corresponding to the amount of blood to be supplied can be secured in the blood filter 2. The volume of the space 82 is set to be 1.2 to 3.0 times (e.g., 100 to 250 μL) as much as the amount of blood used for a blood inspection (e.g., 50 to 200 μL).

As explained above, according to the blood inspecting apparatus 1, by detecting the position of the interface In at the flow rate sensor 53, the amount of discharged isotonic sodium chloride solution from the blood filter 2 is regulated. Accordingly, in comparison with a case in which the amount of discharged isotonic sodium chloride solution is regulated by the liquid-level detecting sensor at the blood supply nozzle like the case of the conventional blood inspecting apparatus, it is possible for the blood inspecting apparatus 1 to regulate the amount of discharged isotonic sodium chloride solution (accomplishment of a proper interface position) within a short time. Therefore, it becomes possible to shorten a time necessary for a blood inspection.

Figure 21:
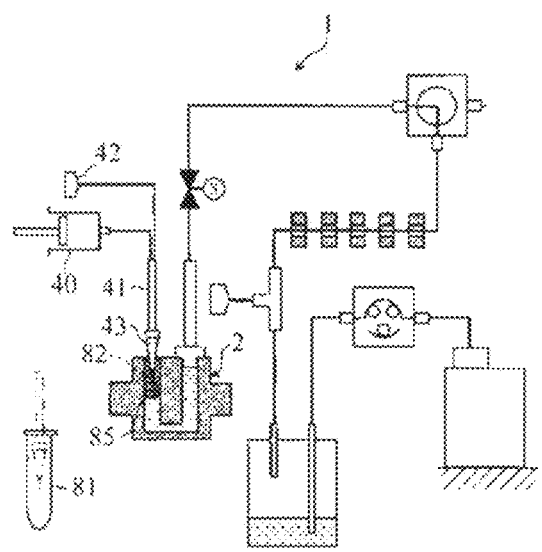
FIG. 21 is a piping diagram for explaining a blood supply operation to the blood filter in the blood inspecting apparatus shown in FIG. 1.
Figure 22A:
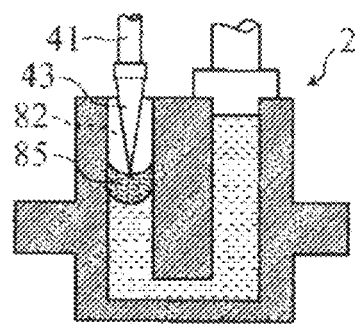
FIGS. 22A and 22B are cross-sectional views around the blood filter for explaining the blood supply operation.
Figure 22B:
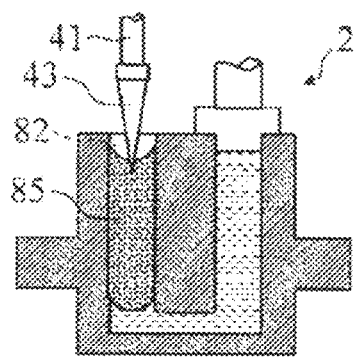

Next, as shown in FIG. 21, the controller 10 (see FIG. 14) supplies a blood 85 to the space 82 provided in the blood filter 2. More specifically, the controller 10 (see FIG. 14) suctions a blood from the blood collecting tube 81 into the interior of the chip 43 attached to the blood supply nozzle 41 by utilizing power by the sampling pump 40, and delivers the blood 85 in the chip 43 to the space 82 in the blood filter 2 as shown in FIGS. 22A and 22B. The delivery amount of blood 85 with respect to the blood filter 2 is set to be an amount corresponding to the volume of the space 82, and the delivery amount is controlled by causing the liquid-level detecting sensor 42 (see FIG. 21) to detect the liquid level of the blood in the interior of the chip 43.

Figure 23:
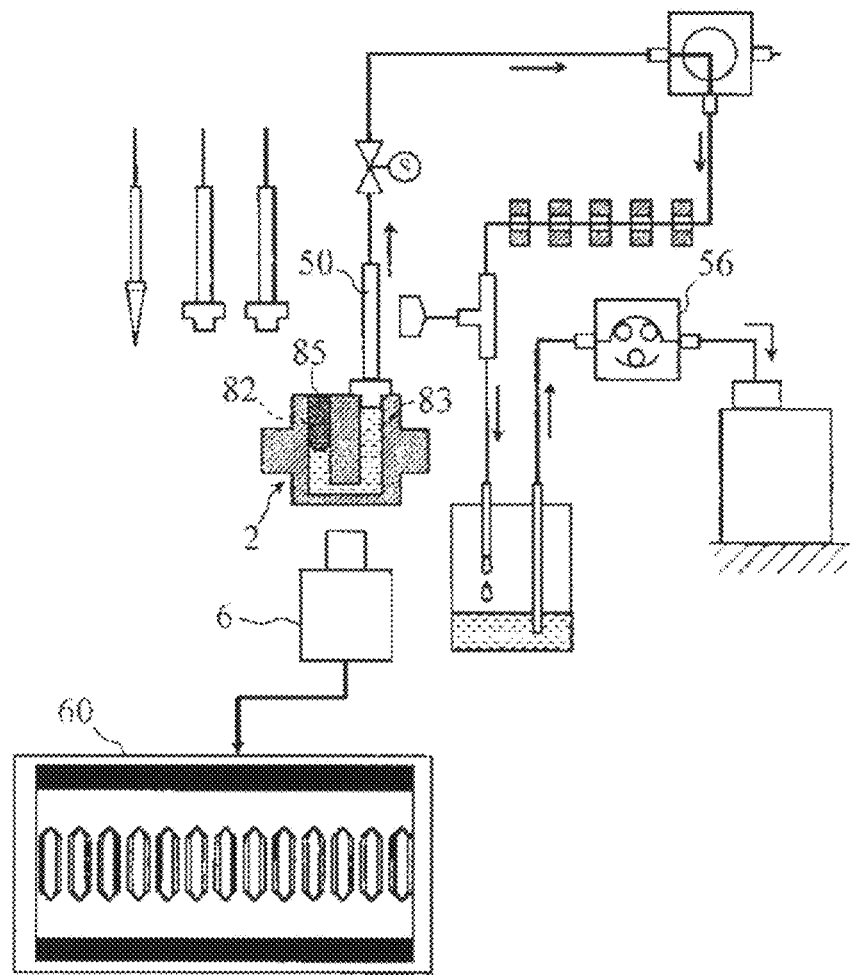
FIG. 23 is a piping diagram for explaining a measuring operation by the blood inspecting apparatus shown in FIG. 1.

Next, according to the blood inspecting apparatus 1, as shown in FIG. 23, the blood 85 supplied to the space 82 in the blood filter 2 is inspected. More specifically, the controller 10 (see FIG. 14) discharges the isotonic sodium chloride solution 83 in the blood filter 2 through the liquid discharging nozzle 50 by utilizing power by the pressure-reduction pump 56. At this time, in the blood filter 2, the blood 85 is moved together with the isotonic sodium chloride solution 83.

More specifically, in the blood filter 2, the blood 85 passes through a fluid channel (see FIGS. 6 to 9) formed between the fluid-channel substrate 21 and the transparent cover 23, and is moved to the small-diameter cylinder 25B. In the fluid-channel substrate 21, as is explained with reference to FIGS. 6 to 9, the blood 85 is inlet into the inlet fluid channel 28B through the through hole 28D, successively travels the communicating grooves 29 and the discharging fluid channel 28C, and is discharged through the through hole 28E. When the width dimension of the communicating groove 29 is set to be smaller than the diameter of a cell like a blood cell or a blood platelet in the blood 85, the cell travels the communicating groove 29 while deforming, or causes the communicating groove 29 to be clogged. Such a condition of the cell is subjected to an imaging by the imaging device 6. An imaging result by the imaging device 6 may be displayed on the monitor 60 in real time or may be displayed on the monitor 60 after recorded.

On the other hand, as shown in FIG. 11, at the flow rate sensor 53, the interface In traveling in the straight tube 59 is detected. The operating unit 11 (see FIG. 14) determines whether or not the interface In passes through based on pieces of information obtained from individual photo sensors 58A to 58E and calculates a travel time of the interface In. Because the travel time of the interface In corresponds to a travel time of the blood 85 in the blood filter 2, i.e., the flowability (resistance) of the blood 85, the condition of the blood 85 can be figured out based on the travel time of the interface In.

The flow rate sensor 53 comprises the straight tube 59 arranged horizontally, so that no water head difference at the flow rate sensor changes at the time of a blood inspection unlike the flow rate sensor using a U-tube. Accordingly, in the blood inspecting apparatus 1, it is possible to prevent any measurement error inherent to a change in the water head difference at the time of a blood inspection, thereby enabling improvement of the measurement precision.

Figure 24:
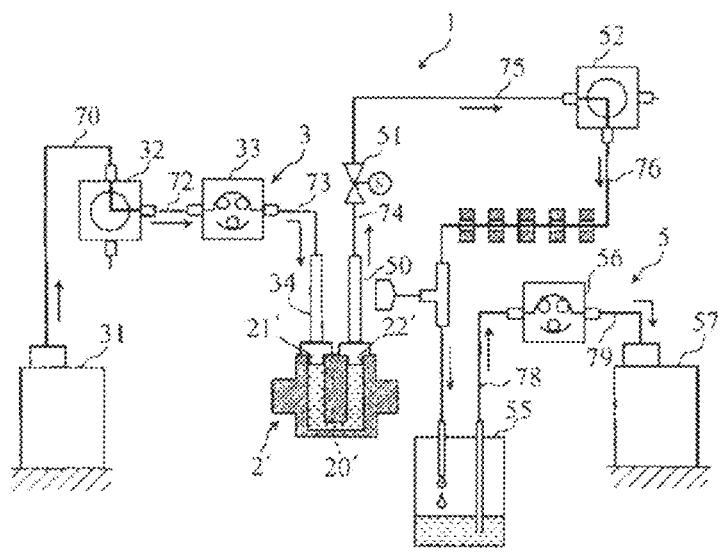
FIG. 24 is a piping diagram for explaining a rinsing operation for a piping in the blood inspecting apparatus shown in FIG. 1.

As shown in FIG. 24, when inspection of the blood completes, based on a selection given by the user, the pipings 74 to 77 of the liquid discharging mechanism 5 are rinsed. This rinsing process is carried out as the user selects a rinsing mode with a dummy chip 2' being set at the position where the blood filter 2 is set. The dummy chip 2' has the same external shape as that of the blood filter 2, and has a communicating hole 20' provided therein. The communicating hole 20' has openings 21', 22' provided at respective portions corresponding to the upper openings 25Aa, 25Ba of the small-diameter cylinders 25A, 25B (see FIGS. 2 and 3) in the blood filter 2.

In the blood inspecting apparatus 1, when the rinsing mode is selected, the controller 10 (see FIG. 14) first attaches the liquid supply nozzle 34 of the liquid supply mechanism 3 to the opening 21' of the communicating hole 20' of the dummy chip 2', and attaches the liquid discharging nozzle 50 of the liquid discharging mechanism 5 to the opening 22' of the communicating hole 20' of the dummy chip 2'. On the other hand, the controller 10 (see FIG. 14) switches the three-way valve 32 to make the bottle 31 communicated with the liquid supply nozzle 34, and switches the three-way valve 52 and opens the electromagnetic valve 51 to make the liquid discharging nozzle 50 communicated with the pressure-reduction bottle 55. That is, a path between the bottle 31 and the pressure-reduction bottle 55 is communicated through the communicating hole 20' of the dummy chip 2'. In this state, the controller 10 (see FIG. 14) actuates the pressurizing pump 33 of the liquid supply mechanism 3 and the pressure-reduction pump 56 of the liquid discharging mechanism 5. The pressure by the pressurizing pump 33 is set to be, for example, 1 to 150 kPa, and the reduced pressure by the pressure-reduction pump 56 is set to be 0 to −50 kPa.

When the pressurizing pump 33 and the pressure-reduction pump 56 are actuated in this fashion, the distilled water in the liquid bottle 31 is supplied to the liquid supply nozzle 34 through the pipings 70, 72, and 73, passes through the communicating hole 20' of the dummy chip 2', and is discharged in the pressure-reduction bottle 55 through the liquid discharging nozzle 50 and the pipings 74 to 77. The distilled water discharged in the pressure-reduction bottle 55 is discharged in the liquid discharging bottle 57 through the pipings 78, 79 by power of the pressure-reduction pump 56. Accordingly, the pipings 74 to 77 in the liquid discharging mechanism 5 are rinsed by the distilled water.

According to the blood inspecting apparatus 1, the condition of the blood is figured out based on information from the flow rate sensor 53 provided at the downstream side of the blood filter 2. Accordingly, unlike the conventional blood inspecting apparatus, it is not necessary to separately provide a piping and a nozzle interconnecting the flow rate sensor 53 and the blood filter 2 from the pipings 74 to 79 of the liquid discharging mechanism 5 and the liquid discharging nozzle 50. As a result, the blood inspecting apparatus 1 can have a apparatus configuration simplified, and can be manufactured with an advantage in cost, and can be miniaturized. Moreover, because the number of nozzles and the valves subjected to drive control is reduced, the mean-time-between-failure (MTBF) can be extended. Furthermore, because the flow rate sensor 53 is provided at the halfway of the piping of the liquid discharging mechanism 5, it is not necessary to separately provide a piping for the flow rate sensor 53 from the pipings 74 to 79 of the liquid discharging mechanism 5, and the piping length necessary for a blood inspection can be shortened. Accordingly, the fluid resistance at the time of a blood inspection can be reduced, so that it becomes possible to set power necessary for actuating the pressure-reduction pump 56 at the time of a blood inspection to be small. This results in reduction of the running cost.

Figure 25:
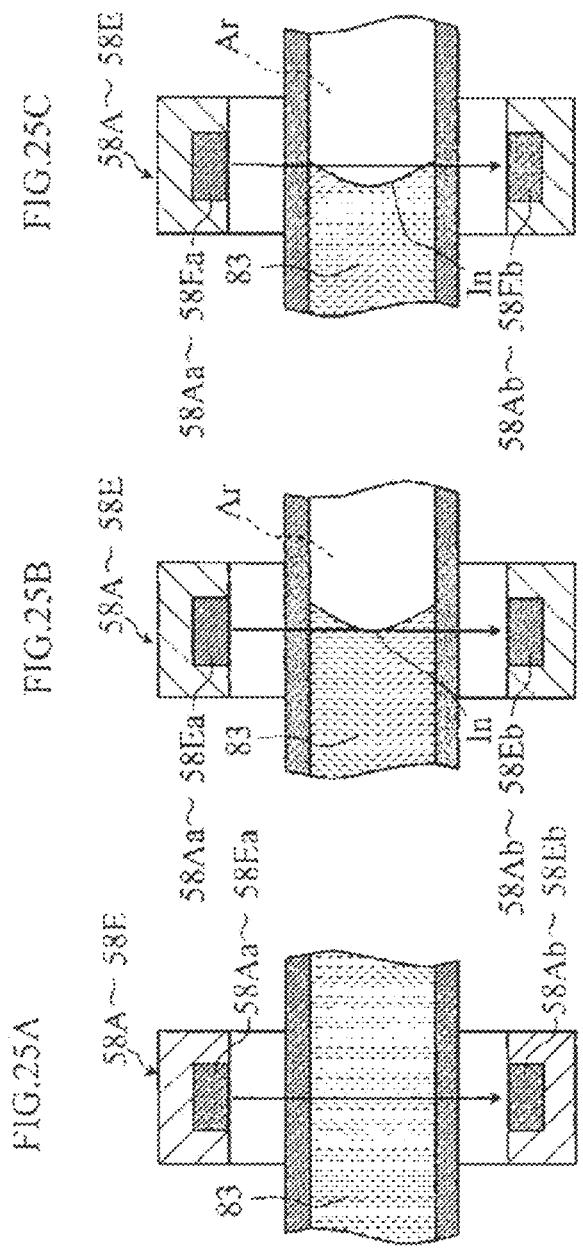
FIGS. 25A to 25C are cross-sectional views of a flow rate sensor corresponding to FIGS. 12A to 12C, respectively, for explaining another illustrative process of inletting air in a piping in a blood inspecting method according to the present invention.

Next, an explanation will be given of another example of a process of inletting the air in the piping and that of a process of securing a space for supplying a blood to the blood filter with reference to the drawings referred so far and FIGS. 25 to 27 as needed.

As shown in FIG. 16, in inletting of the air Ar into the piping 76, first, the controller 10 (see FIG. 14) closes the electromagnetic valve 51 and stops actuating the pressure-reduction pump 56, and switches the three-way valve 52 into a state shown in FIG. 17B from a state shown in FIG. 17A, to cause the piping 76 to be communicated with the atmosphere through the piping 7A. On the other hand, the controller 10 (see FIG. 14) actuates the pressure-reduction pump 56. Accordingly, the piping 7A and the piping 76 are subjected to pressure reduction, and as shown in FIGS. 17B and 17C, the air Ar is inlet into the piping 76 through the piping 7A. Such inletting of the air Ar into the piping 76 is carried out until the target amount of air Ar is inlet into the piping 76. Inletting of the air into the piping 76 is terminated when, as shown in FIG. 16, while the pressure of the piping 77 is being monitored by the pressure sensor 54, the pressure detected by the pressure sensor 54 becomes a predetermined value by switching the three-way valve 52 to the electromagnetic-valve-51 side. At this time, because the electromagnetic valve 51 is closed, travelling of the air Ar (see FIG. 17C) inlet in the piping 76 is rapidly terminated.

The inlet amount of air with respect to the piping 76 is set in such a way that the travel amount (waste liquid amount) of the interface In between the inlet air Ar and the isotonic sodium chloride solution 83 reaching a position detected by the photo sensor 58A of the flow rate sensor 53 matches or substantially matches the supply amount of blood to the blood filter 2 (see FIGS. 19B and 20B). That is, unlike the example explained previously, the piping 76 is not completely replaced with the air Ar, and a residual air is present in the interior of the piping 76.

According to the above-explained embodiment, when the air Ar is inlet into the piping 76, the pressure sensor 54 monitors the pressure of the piping 77, to regulate the inlet amount of air Ar, but the flow rate sensor 53 may monitor the position of the air Ar, and the inlet amount of air Ar may be regulated based on that monitoring result, or the pressure of the piping 76 may be monitored to regulate the inlet amount of air Ar.

Figure 26:
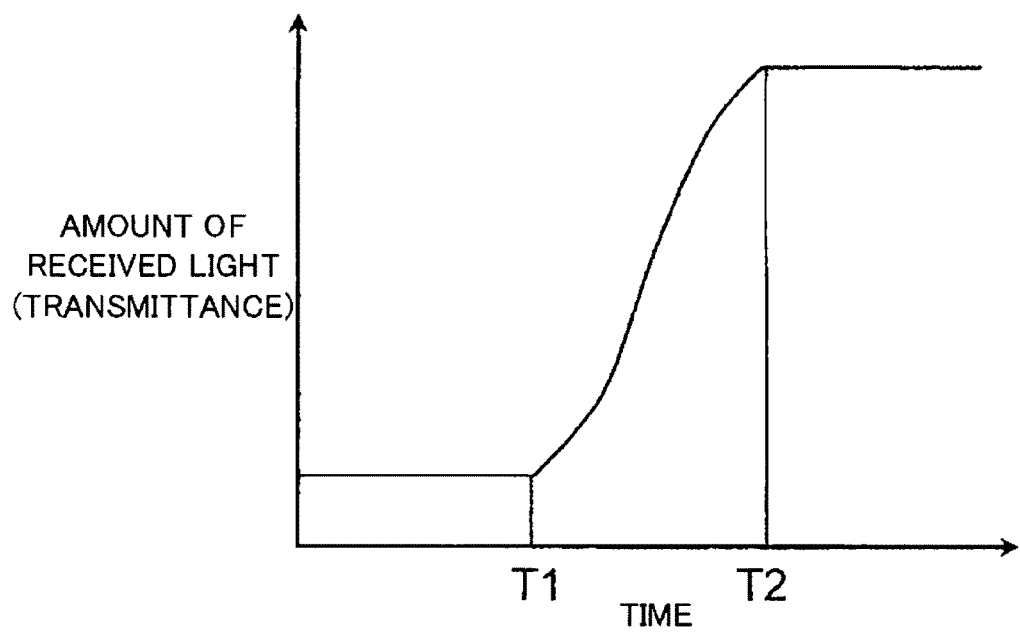
FIG. 26 is a graph showing illustrative optical information obtained by each photo sensor of the flow rate sensor in the air inletting operation.

As shown in FIGS. 25A and 25B, when the air Ar (interface In) travels the straight tube 59, the ratio between the isotonic sodium chloride solution 83 and the air Ar at a region corresponding to each photo sensor 58A to 58E gradually changes, so that as shown in FIG. 26, the amount of received light (transmittance) obtained by each photo sensitive device 58Ab to 58Eb in the photo sensor 58A to 58E also changes. Accordingly, based on a time T1 when the amount of received light (transmittance) obtained by the photo sensor 58A to 58E starts changing, or a time T2 when the amount of received light (transmittance) becomes constant after the amount of received light (transmittance) has started changing, it is possible to detect that the air Ar (interface In) reaches. Moreover, if reaching of the air Ar at plural photo sensors 58A to 58E is individually detected, a time when the air Ar (interface In) passes through between adjoining photo sensors 58A to 58E, i.e., a travel time of the air Ar (interface In) can be detected. Furthermore, by providing equal to or greater than three photo sensors 58A to 58E, it is possible to measure not only the travel time of the air Ar (interface In) at a certain time but also a change in the travel time of the air Ar (interface In) along with advancement of time.

Figure 27A:
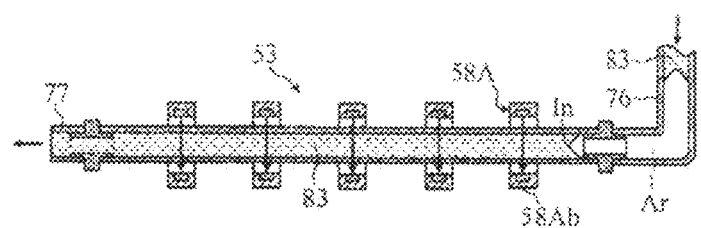
FIGS. 27A and 27B are cross-sectional views corresponding to FIGS. 20A, 20B, respectively, and showing a state around the flow rate sensor for explaining another illustrative process of forming a space for supplying a blood to the blood filter.
Figure 27B:
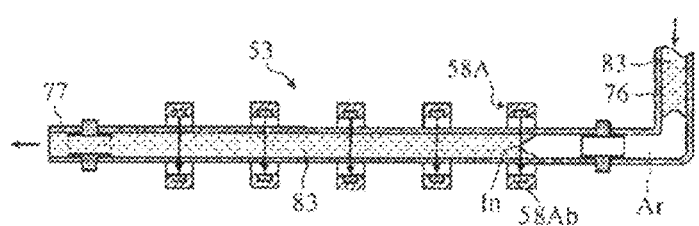
Figure 28:
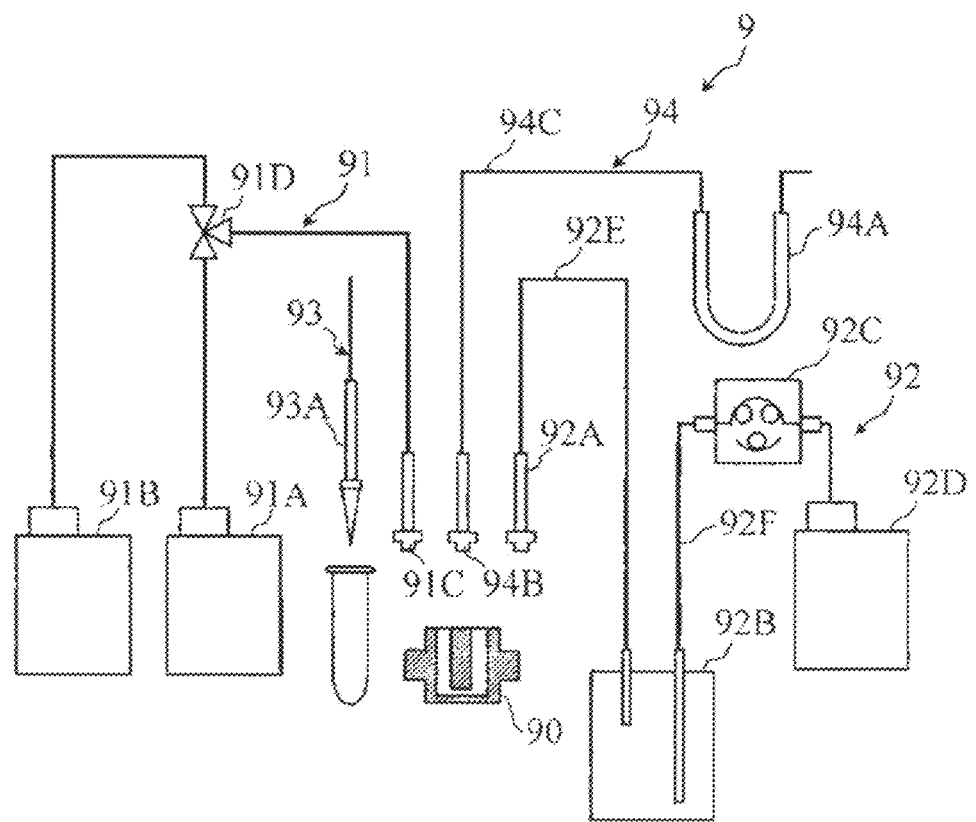
FIG. 28 is a piping diagram showing an illustrative conventional blood inspecting apparatus.
Figure 29:
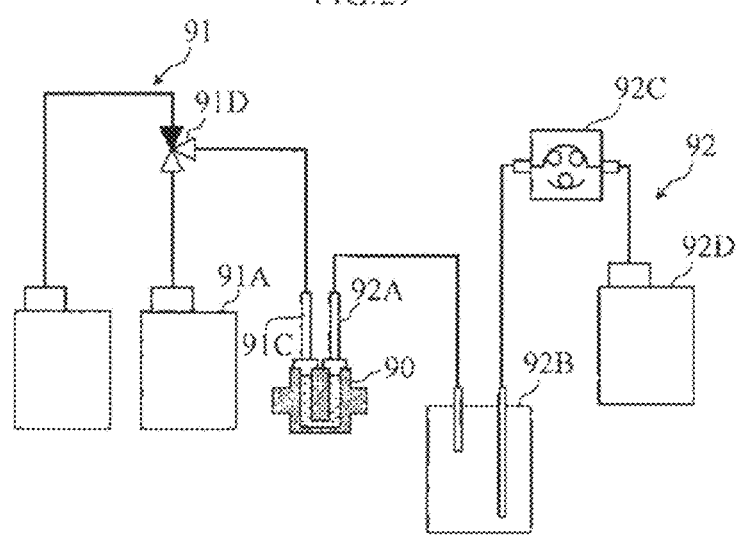
FIG. 29 is a piping diagram for explaining a gas/liquid replacement operation by the blood inspecting apparatus shown in FIG. 28.
Figure 31A:
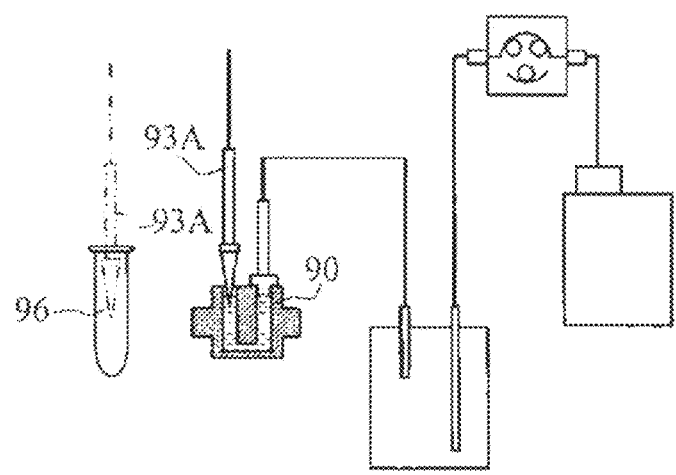
FIG. 31A is a piping diagram for explaining a blood supply operation to the blood filter in the blood inspecting apparatus shown in FIG. 28.
Figure 31B:
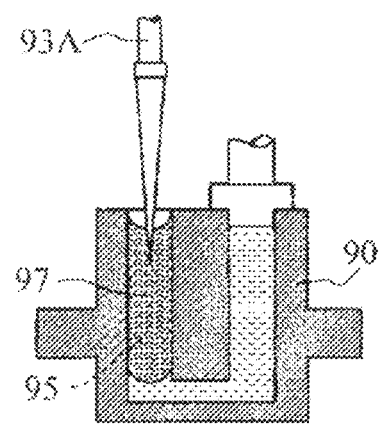
FIG. 31B is a cross-sectional view around the blood filter for explaining the blood supply operation.
Figure 32A:
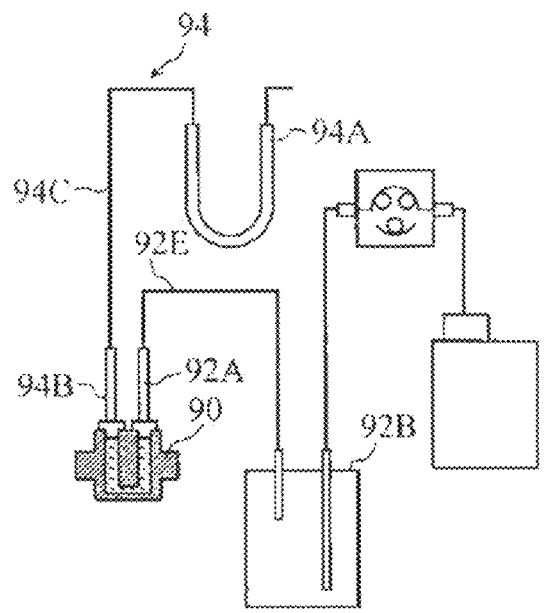
FIG. 32A is a piping diagram for explaining a measuring operation by the blood inspecting apparatus shown in FIG. 28.
Figure 32B:
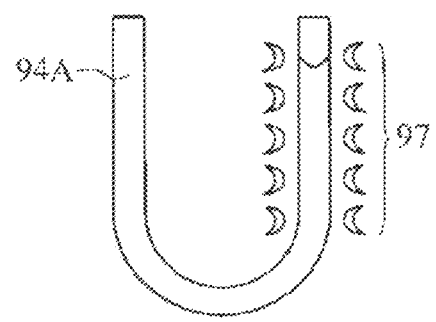
FIG. 32B is a front view for explaining a fluid-channel sensor in the measuring operation.

Regarding securing of the space 82 necessary for supplying the blood to the blood filter 2, the controller 10 (see FIG. 14) detaches the liquid supply nozzle 34 from the blood filter 2, opens the electromagnetic valve 51, and actuates the pressure-reduction pump 56. Accordingly, as shown in FIGS. 19A and 19B, the isotonic sodium chloride solution in the interior of the blood filter 2 is suctioned and eliminated through the liquid discharging nozzle 50, and an air 84 is inlet into the blood filter 2. At this time, as shown in FIGS. 27A and 27B, the isotonic sodium chloride solution 83 in the pipings 76, 77 is caused to travel toward the pressure-reduction bottle 55 (see FIG. 18), and together with this travelling, the air Ar in the piping 76 also travels toward the pressure-reduction bottle 55 (see FIG. 18).

On the other hand, at the photo sensor 58A of the flow rate sensor 53, it is detected whether or not the air Ar (interface In) reaches thereto. As explained above, when the air Ar (interface In) passes through the photo sensor 58A, the amount of received light by the photo sensitive device 58Ab becomes large, so that the photo sensor 58A can detect that the air Ar (interface In) reaches thereto. When the photo sensor 58A detects that the air Ar (interface In) reaches thereto, the controller 10 (see FIG. 14) closes the electromagnetic valve 51 (see FIG. 18), to terminate travelling of the isotonic sodium chloride solution 83 and the air Ar.

As explained above, the inlet amount of air Ar with respect to the piping 76 is set in such a way that the travel amount (waste liquid amount) of the interface In between the inlet air Ar and the isotonic sodium chloride solution 83 reaching the position detected by the photo sensor 58A of the flow rate sensor 53 matches or substantially matches the supply amount of blood to the blood filter 2 after the air Ar is inlet into the piping 76. That is, because the inlet amount of air (the position of the interface between the isotonic sodium chloride solution and the air) with respect to the piping 76 is regulated beforehand, when the air Ar reaches the position detected by the photo sensor 76 (see FIG. 20B), the space 82 formed in the blood filter 2 has a volume matching or substantially matching the amount of blood to be supplied to the blood filter 2 (see FIG. 19B).

As explained above, according to the blood inspecting apparatus 1, as the flow rate sensor 53 detects the position of the air Ar (interface In), the discharge amount of isotonic sodium chloride solution from the blood filter 2 is regulated. Accordingly, in comparison with a case in which the discharge amount of isotonic sodium chloride solution is regulated by the liquid-level detecting sensor of the blood supply nozzle like the conventional blood inspecting apparatus, the blood inspecting apparatus 1 can regulate the discharge amount of isotonic sodium chloride solution (accomplishment of a proper interface position) within a short time. Therefore, it is possible to shorten a time necessary for a blood inspection.

The present invention is not limited to the foregoing embodiment, and can be changed and modified in various forms. For example, the present invention can be applied to a case in which characteristics, such as a viscosity and a grain size distribution, are inspected using not only a blood with a blood cell but also a sample, such as overall liquids with grains, or one with no grain but with an equal to or larger than a certain level of viscosity. More specifically, the present invention can be applied to cases in which it is inspected whether or not a desired viscosity is ensured in a sample needing an equal to or larger than certain level of viscosity, e.g., an adhesive like a bond for woods, in which it is inspected whether or not a viscosity corresponding to a desired eating texture is ensured in foods like a jelly, and in which a sample having powders dispersed in a solvent in order to inspect whether or not the particle size distribution of the powders is within a desired range.

Moreover, as the flow rate sensor, a curved tube instead of the straight tube can be used, or, conductive or dielectric capacitance type can be used instead of the plural photo sensors. The conductive type sensor unit electrically detects whether or not a space between an individual electrode and a ground electrode becomes a liquid junction state by a liquid, thereby detecting an interface (presence/absence of a liquid or presence/absence of air) between the air and the liquid. On the other hand, the dielectric capacitance type sensor unit detects an interface (presence/absence of a liquid or presence/absence of air) between the air and the liquid based on a change in an electrostatic capacitance between an individual electrode and a ground electrode.

The invention claimed is:

1. An analysis method using an analysis apparatus comprising a resistive body, a supply piping that is provided at an upstream side of the resistive body and supplies a liquid to the resistive body, a pressurizing pump that is provided at a halfway of the supply piping, a discharging piping that is connected to the resistive body and discharges the liquid supplied to the resistive body, a flow rate sensor that is arranged at a halfway of the discharging piping of the resistive body, a pressure-reduction pump that is provided at a downstream side of the resistive body and through the discharging piping, and a pressure-reduction bottle that is arranged between the flow rate sensor and the pressure-reduction pump and is connected to the pressure-reduction pump, the analysis method comprising:

a first step of driving the pressurizing pump and the pressure-reduction pump, of reducing a pressure in the pressure-reduction bottle, and of filling the liquid from the supply piping in an interior of the resistive body through which a sample passes;

a second step of discharging, from the discharging piping, some of the liquid filled in the interior of the resistive body, and of securing a space in the interior of the resistive body for filling the sample;

a third step of supplying the sample into the space;

a fourth step of causing the sample to travel in the interior of the resistive body; and a fifth step of measuring a travel time of the sample in the interior of the resistive body by using the flow rate sensor.

2. The analysis method according to claim 1, wherein as the flow rate sensor, a sensor including a tubular body and a sensor unit with a plurality of detecting areas for detecting an interface between the liquid and air travelling in the tubular body is used, and the analysis method further comprises a sixth step of inletting air into the tubular body, the sixth step being executed between the first step and the second step.

* * * * *